(12) United States Patent
Cowan et al.

(10) Patent No.: US 10,413,330 B2
(45) Date of Patent: Sep. 17, 2019

(54) SPINAL IMPLANT SYSTEM AND METHOD

(71) Applicant: Warsaw Orthopedic, Inc, Warsaw, IN (US)

(72) Inventors: Benjamin David Cowan, Memphis, TN (US); Robert A. Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 92 days.

(21) Appl. No.: 15/232,537

(22) Filed: Aug. 9, 2016

(65) Prior Publication Data
US 2018/0042647 A1 Feb. 15, 2018

(51) Int. Cl.
*A61B 17/70* (2006.01)

(52) U.S. Cl.
CPC ...... *A61B 17/7043* (2013.01); *A61B 17/7037* (2013.01); *A61B 17/7052* (2013.01)

(58) Field of Classification Search
CPC ............ A61B 17/7032; A61B 17/7037; A61B 17/7041; A61B 17/7043
See application file for complete search history.

(56) References Cited

U.S. PATENT DOCUMENTS

| | | | |
|---|---|---|---|
| 5,002,542 A | 3/1991 | Frigg | |
| 5,053,034 A | 10/1991 | Olerud | |
| 5,154,719 A * | 10/1992 | Cotrel | A61B 17/7002 606/308 |
| 5,261,907 A * | 11/1993 | Vignaud | A61B 17/7052 606/252 |
| 5,397,363 A * | 3/1995 | Gelbard | A61B 17/7032 606/250 |
| 5,474,551 A | 12/1995 | Finn et al. | |
| 5,562,662 A * | 10/1996 | Brumfield | A61B 17/7002 606/279 |
| 5,645,544 A | 7/1997 | Tai et al. | |
| 5,888,221 A * | 3/1999 | Gelbard | A61B 17/7032 606/264 |
| 6,183,473 B1 | 2/2001 | Ashman | |
| 6,231,575 B1 | 5/2001 | Krag | |
| 6,264,658 B1 * | 7/2001 | Lee | A61B 17/7002 606/252 |
| 6,520,962 B1 | 2/2003 | Taylor et al. | |
| 6,551,318 B1 | 4/2003 | Stahurski | |
| 6,602,253 B2 | 8/2003 | Richelsoph et al. | |
| 6,875,211 B2 | 4/2005 | Nichols et al. | |
| 7,621,941 B2 | 11/2009 | Schlapfer et al. | |
| 7,648,520 B2 * | 1/2010 | Markworth | A61B 17/7005 606/246 |
| 7,674,293 B2 | 3/2010 | Kuiper et al. | |
| 7,722,648 B2 * | 5/2010 | Drewry | A61B 17/7052 606/250 |
| 7,789,899 B2 * | 9/2010 | Markworth | A61B 17/7005 606/286 |
| 7,799,059 B2 | 9/2010 | Kramer et al. | |

(Continued)

*Primary Examiner* — Jacqueline T Johanas

(57) ABSTRACT

A spinal construct comprises a fastener including a first portion defining an implant cavity and a second portion configured to penetrate tissue. A member defines a cavity configured for disposal of at least a portion of the first portion. The member includes an implant engaging surface fixable within the implant cavity and connected to a connecting element fixable adjacent the first portion. Systems and methods of use are disclosed.

21 Claims, 14 Drawing Sheets

(56) References Cited

U.S. PATENT DOCUMENTS

| | | | |
|---|---|---|---|
| 7,806,912 B2 | 10/2010 | Lawton et al. | |
| 7,837,714 B2* | 11/2010 | Drewry | A61B 17/7052 606/250 |
| 7,867,255 B2* | 1/2011 | Miller | A61B 17/705 606/250 |
| 8,021,399 B2 | 9/2011 | Ritland | |
| 8,167,908 B2 | 5/2012 | Ely et al. | |
| 8,221,473 B2* | 7/2012 | Butler | A61B 17/7037 606/264 |
| 8,246,657 B1 | 8/2012 | Samuel | |
| 8,273,086 B2* | 9/2012 | Serhan | A61B 17/0642 606/75 |
| 8,337,532 B1 | 12/2012 | McLean et al. | |
| 8,353,934 B2* | 1/2013 | Drewry | A61B 17/7052 606/250 |
| 8,353,937 B2* | 1/2013 | Capote | A61B 17/7032 606/246 |
| 8,758,411 B1 | 6/2014 | Rayon et al. | |
| 8,870,922 B2* | 10/2014 | Hammer | A61B 17/7049 606/250 |
| 8,882,803 B2 | 11/2014 | Iott et al. | |
| 8,945,186 B2* | 2/2015 | Walker | A61B 17/7052 606/250 |
| 8,998,956 B2 | 4/2015 | George et al. | |
| 8,998,957 B2 | 4/2015 | Kalfas et al. | |
| 9,101,405 B2 | 8/2015 | Dickenson et al. | |
| 9,198,696 B1* | 12/2015 | Bannigan | A61B 17/7052 |
| 9,408,641 B2* | 8/2016 | Zhang | A61B 17/7023 |
| 9,451,994 B1 | 9/2016 | Whipple et al. | |
| 9,510,862 B2 | 12/2016 | Montello et al. | |
| 2002/0007183 A1* | 1/2002 | Lee | A61B 17/7002 606/252 |
| 2004/0210216 A1 | 10/2004 | Farris et al. | |
| 2005/0131410 A1* | 6/2005 | Lin | A61B 17/7032 606/266 |
| 2005/0177154 A1* | 8/2005 | Moumene | A61B 17/7032 606/276 |
| 2005/0234451 A1* | 10/2005 | Markworth | A61B 17/7005 606/60 |
| 2006/0064091 A1* | 3/2006 | Ludwig | A61B 17/7007 606/250 |
| 2006/0149237 A1* | 7/2006 | Markworth | A61B 17/7005 606/279 |
| 2006/0229616 A1* | 10/2006 | Albert | A61B 17/7037 606/305 |
| 2006/0247624 A1* | 11/2006 | Banouskou | A61B 17/7037 606/60 |
| 2007/0238335 A1 | 10/2007 | Veldman et al. | |
| 2007/0270808 A1* | 11/2007 | Drewry | A61B 17/7052 606/279 |
| 2007/0270809 A1* | 11/2007 | Drewry | A61B 17/7052 606/279 |
| 2008/0086132 A1* | 4/2008 | Biedermann | A61B 17/7032 606/279 |
| 2009/0036929 A1 | 2/2009 | Reglos et al. | |
| 2011/0087287 A1 | 4/2011 | Reeder et al. | |
| 2011/0190828 A1* | 8/2011 | Null | A61B 17/7041 606/279 |
| 2012/0083851 A1* | 4/2012 | Felix | A61B 17/7037 606/305 |
| 2012/0184997 A1* | 7/2012 | Simonson | A61B 17/7007 606/265 |
| 2014/0350603 A1* | 11/2014 | Purcell | A61B 17/7037 606/265 |
| 2015/0230830 A1* | 8/2015 | Frankel | A61B 17/7043 606/279 |
| 2016/0089187 A1 | 3/2016 | Bootwala et al. | |
| 2017/0079687 A1* | 3/2017 | Oberlander | A61B 17/7037 |
| 2017/0095271 A1 | 4/2017 | Faulhaber | |
| 2017/0112540 A1 | 4/2017 | Montello et al. | |
| 2018/0042647 A1* | 2/2018 | Cowan | A61B 17/7043 |

* cited by examiner

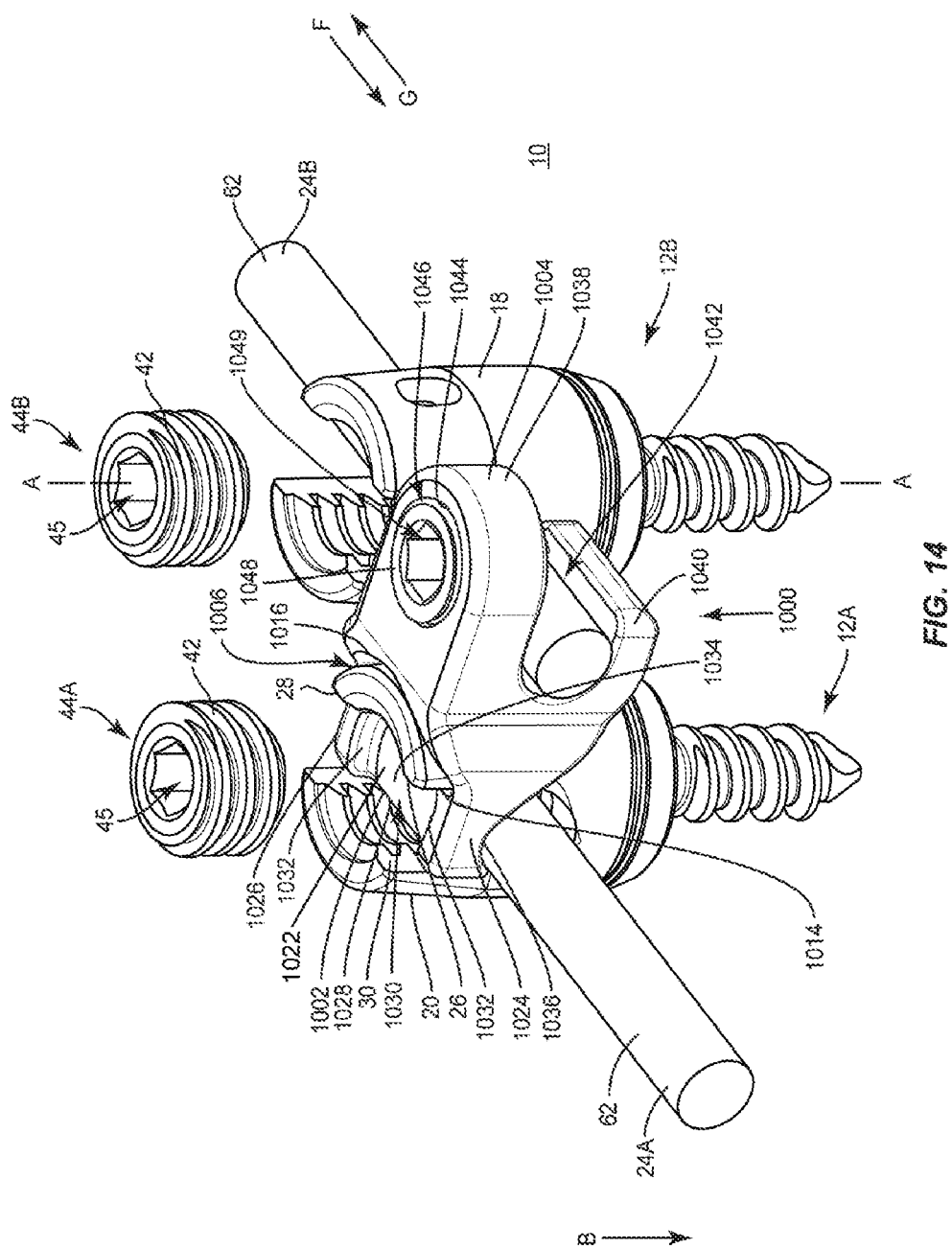

SPINAL IMPLANT SYSTEM AND METHOD

TECHNICAL FIELD

The present disclosure generally relates to surgical implants for the treatment of spinal disorders, and more particularly to a surgical system and method for treatment of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods, connectors and plates can be used to provide stability to a treated region. During surgical treatment, one or more rods may be attached via fasteners to the exterior of two or more vertebral members to provide stability to a treated region. This disclosure describes an improvement over these prior art technologies.

SUMMARY

In one embodiment, a spinal construct is provided. The spinal construct comprises a fastener including a first portion defining an implant cavity and a second portion configured to penetrate tissue. A member defines a cavity configured for disposal of at least a portion of the first portion. The member includes an implant engaging surface fixable within the implant cavity and connected to a connecting element fixable adjacent the first portion. In some embodiments, systems and methods are provided.

BRIEF DESCRIPTION OF THE DRAWINGS

The present disclosure will become more readily apparent from the specific description accompanied by the following drawings, in which:

FIG. 14 is a perspective view of components of one embodiment of a system in accordance with the principles of the present disclosure.

DETAILED DESCRIPTION

Figure 1:
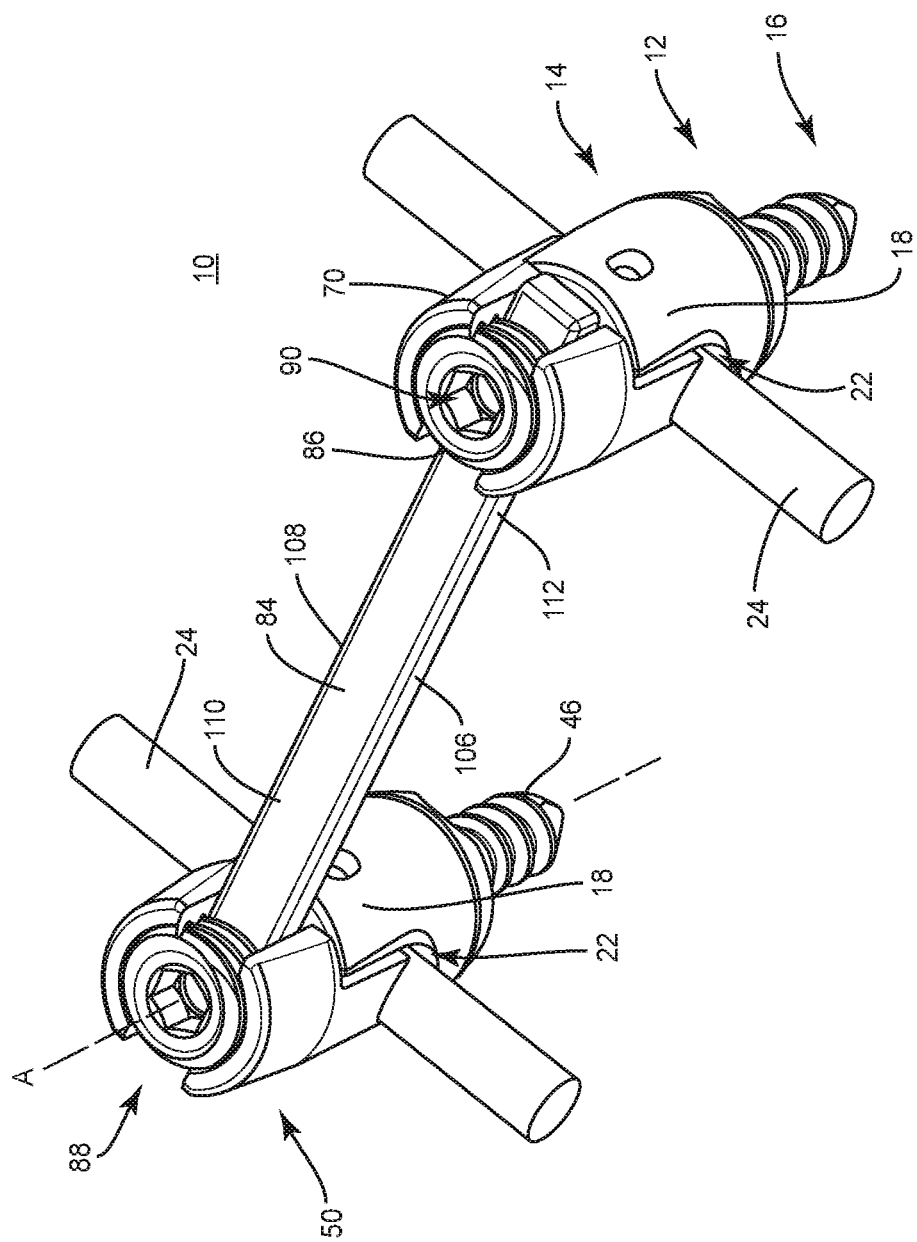
FIG. 1 is a perspective view of components of one embodiment of a system in accordance with the principles of the present disclosure.
Figure 2:
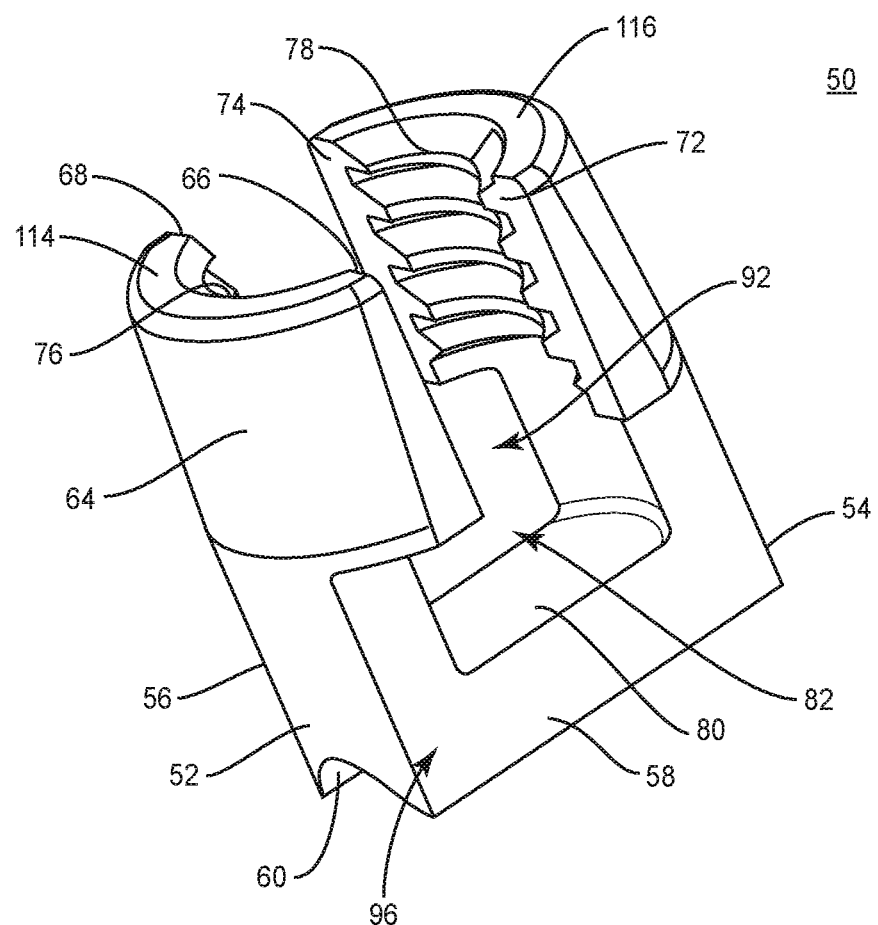
FIG. 2 is a perspective view of a component shown in FIG. 1.
Figure 3:
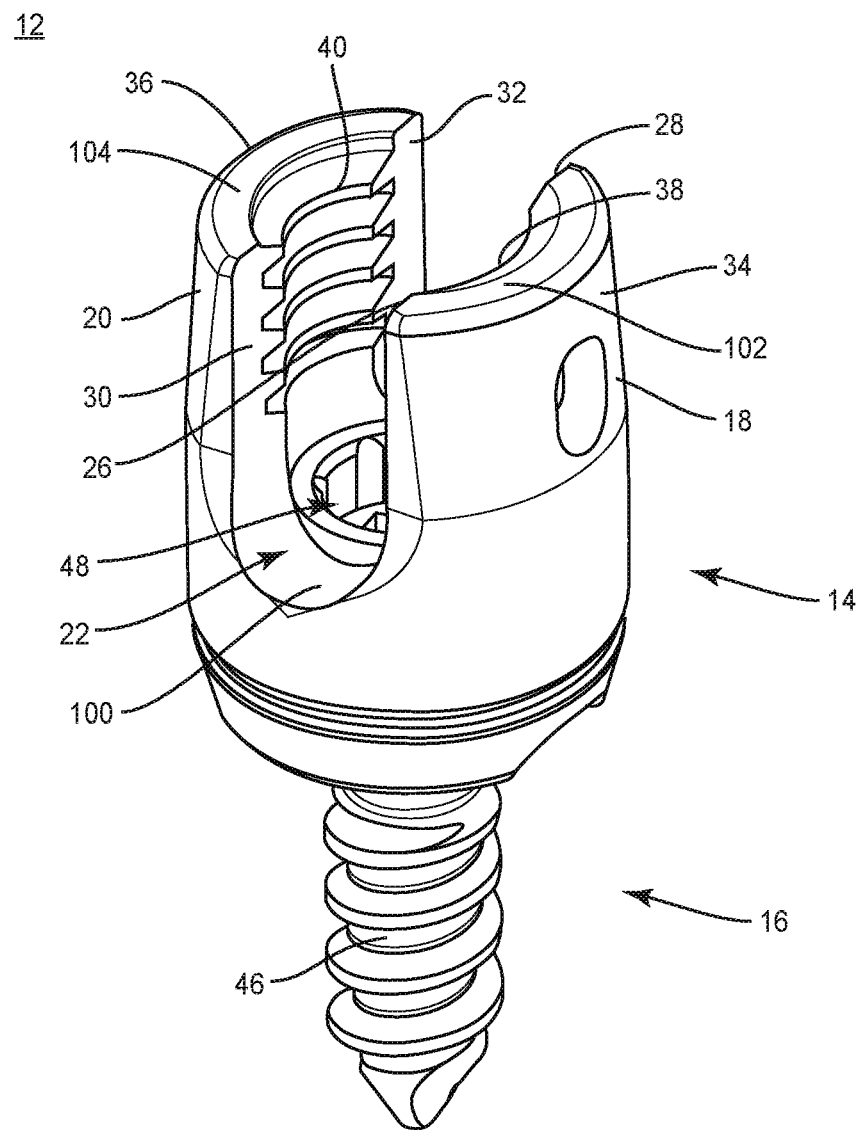
FIG. 3 is a perspective view of components shown in FIG. 1.

The exemplary embodiments of the surgical system and related methods of use disclosed are discussed in terms of medical devices for the treatment of musculoskeletal disorders and more particularly, in terms of a surgical system and method for treatment of a spine disorder. In one embodiment, the systems and methods of the present disclosure are employed with a spinal joint fusion, for example, with a cervical, thoracic, lumbar and/or sacral region of a spine.

In one embodiment, a surgical system is provided that can be employed with methods for attaching a multi-axial screw type connection and rod, which is useful for attachments in the posterior spine where profile and size may prevent other connections. In some embodiments, multiple configurations are presented for attachment to the interconnection in the multi-axial screw rod slot below the rod, above the rod, but below the set screw, and through the set screw.

In one embodiment, the surgical system includes a spinal implant that is employed with methods of connection to a multi-axial screw and rod interconnection. In some embodiments, the interconnection is within the rod slot or rod accepting feature of a multi-axial screw, hook, or other bony attachment anchor and can be below or on top of the rod, or around the set screw or locking member of the interconnection.

In one embodiment, the spinal implant has a low profile and axial size configuration of the connection, which is helpful in reducing the size of constructs while providing versatility in connection. In some embodiments, the spinal implant reduces stress on the rod construct by removing an extra point of fixation on the segmental construct because the interconnection is within an existing interconnection. In some embodiments, this connection is useful when cross-linking and extending from a construct, and/or for screw extension connectors.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Figure 7:
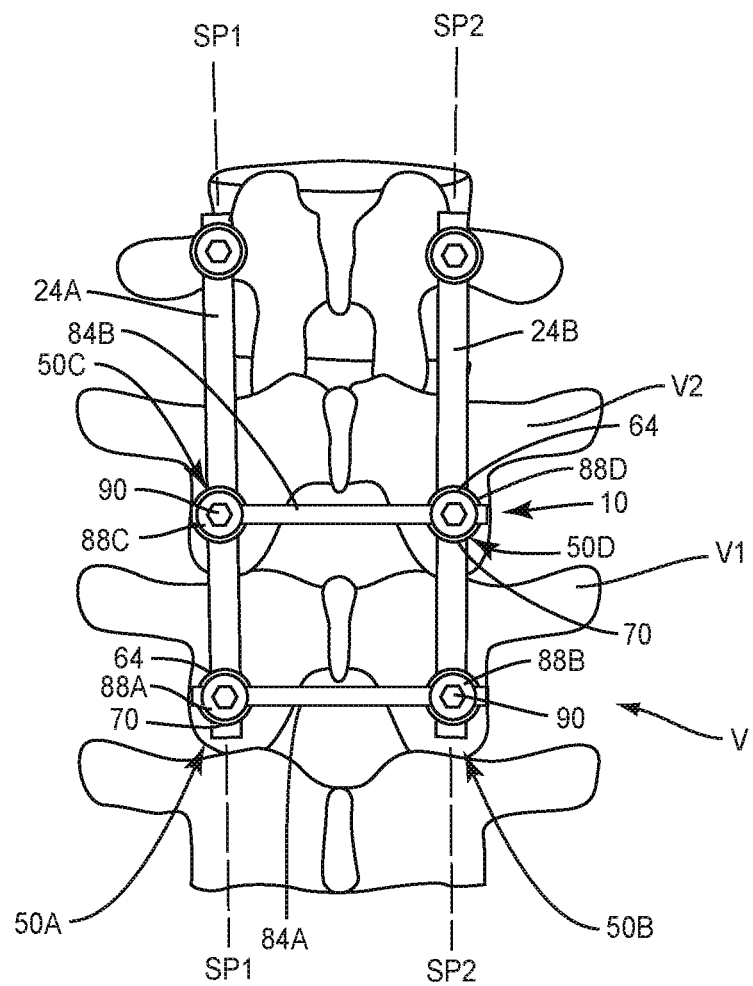
FIG. 7 is a perspective view of components shown in FIG. 1 disposed with vertebrae.

Spinal implant system 10 may be employed, for example, with minimally invasive procedures, including percutaneous techniques, mini-open surgical techniques and/or open surgical techniques to deliver and introduce instrumentation and/or implants, such as, for example, a spinal construct, at a surgical site within a subject body of a patient, which includes, for example, a spine having vertebrae V, as shown, for example, in FIG. 7. In some embodiments, the spinal constructs can include one or more bone fasteners, spinal rods, connectors and/or plates.

Spinal implant system 10 includes a spinal construct comprising a fastener 12 including a first portion, such as, for example, a receiver 14 and a second portion configured to penetrate tissue, such as, for example, a shaft 16. Receiver 14 defines a longitudinal axis A and includes a pair of spaced apart arms 18, 20 that each extend parallel to axis A. Arms 18, 20 define a U-shaped implant cavity 22 therebetween configured for disposal of a spinal implant, such as, for example, a spinal rod 24. Cavity 22 extends perpendicular to axis A In some embodiments, cavity 22 may have various cross section configurations, such as, for example, oval, oblong, triangular, rectangular, square, polygonal, irregular, uniform, non-uniform, variable, tubular and/or tapered. In some embodiments, arm 18, arm 20 and/or cavity 22 may be disposed at alternate orientations, relative to axis A, such as, for example, transverse, perpendicular and/or other angular orientations such as acute or obtuse, co-axial and/or may be offset or staggered. In some embodiments, rod 24 is in alignment with axis A when rod 24 is disposed in cavity 22 such that axis A intersects or extends through rod 24. In some embodiments, system 10 may include one or a plurality of fasteners 12 and/or rods 24.

Arm 18 has a width defined by a distance between a planar side surface 26 and a planar side surface 28. Arm 20 has a width defined by a distance between a planar side surface 30 and a planar side surface 32. An outer surface 34 of arm 18 is convexly curved between surfaces 26, 28. In some embodiments, surface 34 has a continuous radius of curvature between surfaces 26, 28. An outer surface 36 of arm 20 is convexly curved between surfaces 30, 32. In some embodiments, surface 36 has a continuous radius of curvature between surfaces 30, 32. Arm 18 includes a concavely curved inner surface 38 having an internal thread form and arm 20 includes a concavely curved inner surface 40 having an internal thread form. The threads on surfaces 38, 40 are configured to engage an external thread form on an outer surface 42 of a coupling member, such as, for example, a setscrew 44 such that setscrew 44 engages a member, such as, for example, a stirrup 50 to fix an implant-engaging surface 60 of stirrup 50 within cavity 22, as will be discussed.

In some embodiments, surface 40 has a continuous radius of curvature between surfaces 30, 32. In some embodiments, all or only a portion of arm 18 and/or arm 20 may be variously configured and dimensioned, such as, for example, planar, convex, concave, polygonal, irregular, uniform, non-uniform, staggered, tapered, consistent or variable. In some embodiments, setscrew 44 can be variously connected with receiver 14, such as, for example, frictional engagement, mutual grooves, screws, adhesive, nails, barbs and/or raised element.

Shaft 16 is configured with a cylindrical cross section and includes an outer surface 46 having an external thread form. In some embodiments, the thread form on surface 46 may include a single thread turn or a plurality of discrete threads. In some embodiments, the thread form on surface 46 may be self-tapping or intermittent, or may have more than one crest winding about shaft 16. In some embodiments, other engaging structures may be disposed on shaft 16, such as, for example, a nail configuration, barbs, expanding elements, raised elements and/or spikes to facilitate engagement of the shaft with tissue, such as, for example, vertebrae. In some embodiments, all or only a portion of shaft 16 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of surface 46 may have alternate surface configurations to enhance fixation with tissue such as, for example, rough, arcuate, undulating, mesh, porous, semi-porous, dimpled and/or textured.

In some embodiments, surface 46 may include one or a plurality of openings. In some embodiments, all or only a portion of shaft 16 may be cannulated. In one embodiment, shaft 16 may be a screw, or could also be alternatively configured, for example, as a vertebral hook or clamp.

Stirrup 50 extends between an end 52 and an opposite end 54. Stirrup 50 includes opposite planar side surfaces 56, 58 each extending between ends 52, 54. Surfaces 56, 58 extend parallel to one another. An implant engaging surface 60 extends between ends 52, 54 and between surfaces 56, 58. Surface 60 is concavely curved between surfaces 56, 58 and is configured to engage an outer surface 62 of rod 24 to fix rod 24 relative to receiver 14. In some embodiments, surface 60 has a continuous radius of curvature. In some embodiments, all or only a portion of end 52, end 54, surface 56, surface 58 and/or surface 60 may be variously configured and dimensioned, such as, for example, planar, concave, convex, polygonal, irregular, uniform, non-uniform, staggered, tapered, consistent or variable. Surface 60 is in alignment with axis A when stirrup 50 engages fastener 12 such that axis A intersects or extends through surface 60. In some embodiments, surface 60 may have various surface configurations, such as, for example, smooth and/or surface configurations to enhance fixation with rod 24, such as, for example, rough, arcuate, undulating, porous, semi-porous, dimpled, polished and/or textured according to the requirements of a particular application.

Stirrup 50 has a width such that surfaces 30, 32 engage surface 56 and surfaces 26, 28 engage surface 58 when stirrup 50 is inserted within cavity 22, as shown in FIGS. 4-7. Surfaces 30, 32 matingly engage surface 56 and surfaces 26, 28 matingly engage surface 58 to fix stirrup 50 relative to fastener 12. When stirrup 50 is inserted within cavity 22, surface 60 is aligned with a concave inner surface 100 of receiver 14 that, together with surfaces 38, 40, define cavity 22 such that surfaces 60, 100 and define a channel having a cylindrical cross sectional configuration that conforms to that of rod 24. In some embodiments, surface 100 may have various surface configurations, such as, for example, smooth and/or surface configurations to enhance fixation with rod 24, such as, for example, rough, arcuate, undulating, porous, semi-porous, dimpled, polished and/or textured according to the requirements of a particular application.

A proximal portion of end 52 includes an arcuate extension 64 extending between a planar side surface 66 and a planar side surface 68. Surfaces 66, 68 extend parallel to one another. Extension 64 includes an inner surface 76 having an internal thread form. A proximal portion of end 54 includes an arcuate extension 70 extending between a planar side surface 72 that faces surface 66 and a planar side surface 74 that faces surface 68. Surfaces 72, 74 extend parallel to one another. In some embodiments, surfaces 72, 74 extend parallel to surfaces 66, 68. Extension 70 includes an inner surface 78 having an internal thread form.

Surfaces 76, 78 and a transverse surface 80 define a passageway 82 configured for disposal of a connecting element 84. The thread forms on surfaces 76, 78 are configured to engage an external thread form on an outer surface 86 of a coupling member, such as, for example, setscrew 88, such that setscrew 88 engages element 84 to maintain element 84 within passageway 82, as will be described. In some embodiments, all or only a portion of extension 64 and/or extension 70 may be variously configured an dimensioned, such as, for example, planar, concave, convex, polygonal, irregular, uniform, non-uniform, staggered, tapered, consistent or variable. In some embodiments, member 88 can be variously connected with stirrup 50, such as, for example, frictional engagement, mutual grooves, screws, adhesive, nails, barbs and/or raised element.

Stirrup 50 defines a side cavity 92 defined by surface 56 and planar lateral surfaces 94 of extensions 64, 70 that are positioned adjacent surfaces 68, 74. Surfaces 94 extend perpendicular to surfaces 68, 74. Stirrup 50 defines a side cavity 96 defined by surface 58 and planar lateral surfaces 98 of extensions 64, 70 that are positioned adjacent surfaces 66, 72. Surfaces 98 extend perpendicular to surfaces 66, 72. Cavities 92, 98 each define an orthogonal portion of stirrup 50 and are configured for disposal of arms 18, 20 such that cavities 92, 98 matingly engage arms 18, 20, as will be described. In some embodiments, all or only a portion of surfaces 94, 98 may be variously configured and dimensioned, such as, for example, planar, concave, polygonal, irregular, uniform, non-uniform, staggered, tapered, consistent or variable, depending on the requirements of a particular application. In some embodiments, surfaces 94 and/or surfaces 98 may be disposed at alternate orientations, relative to surfaces 68, 74 and/or surfaces 66, 72, such as, for example, transverse, perpendicular and/or other angular orientations such as acute or obtuse, co-axial and/or may be offset or staggered.

Stirrup 50 is inserted within cavity 22 such that surfaces 30, 32 engage surface 56 and surfaces 26, 28 engage surface 58, surface 98 engage a planar top surface 102 of arm 18 and surfaces 94 engage a planar top surface 104 of arm 20, as shown in FIGS. 1 and 4-6. In some embodiments, this configuration prevents stirrup 50 from translating axially relative to receiver 14 in a distal direction while simultaneously preventing stirrup 50 from rotating relative to receiver 14 about axis A. When stirrup 50 is inserted within cavity 22 such that surfaces 30, 32 engage surface 56, surfaces 26, 28 engage surface 58, surfaces 98 engage surface 102 and surfaces 94 engage surface 104, passageway 82 extends perpendicular to cavity 22, as shown in FIGS. 1 and 4-6. In some embodiments, all or only a portion of surfaces 102, 104 may be variously configured and dimensioned, such as, for example, planar, concave, polygonal, irregular, uniform, non-uniform, staggered, tapered, consistent or variable, depending on the requirements of a particular application. In some embodiments, passageway 82 may be disposed at alternate orientations, relative to cavity 22, such as, for example, transverse, perpendicular and/or other angular orientations such as acute or obtuse, co-axial and/or may be offset or staggered.

Figure 6:
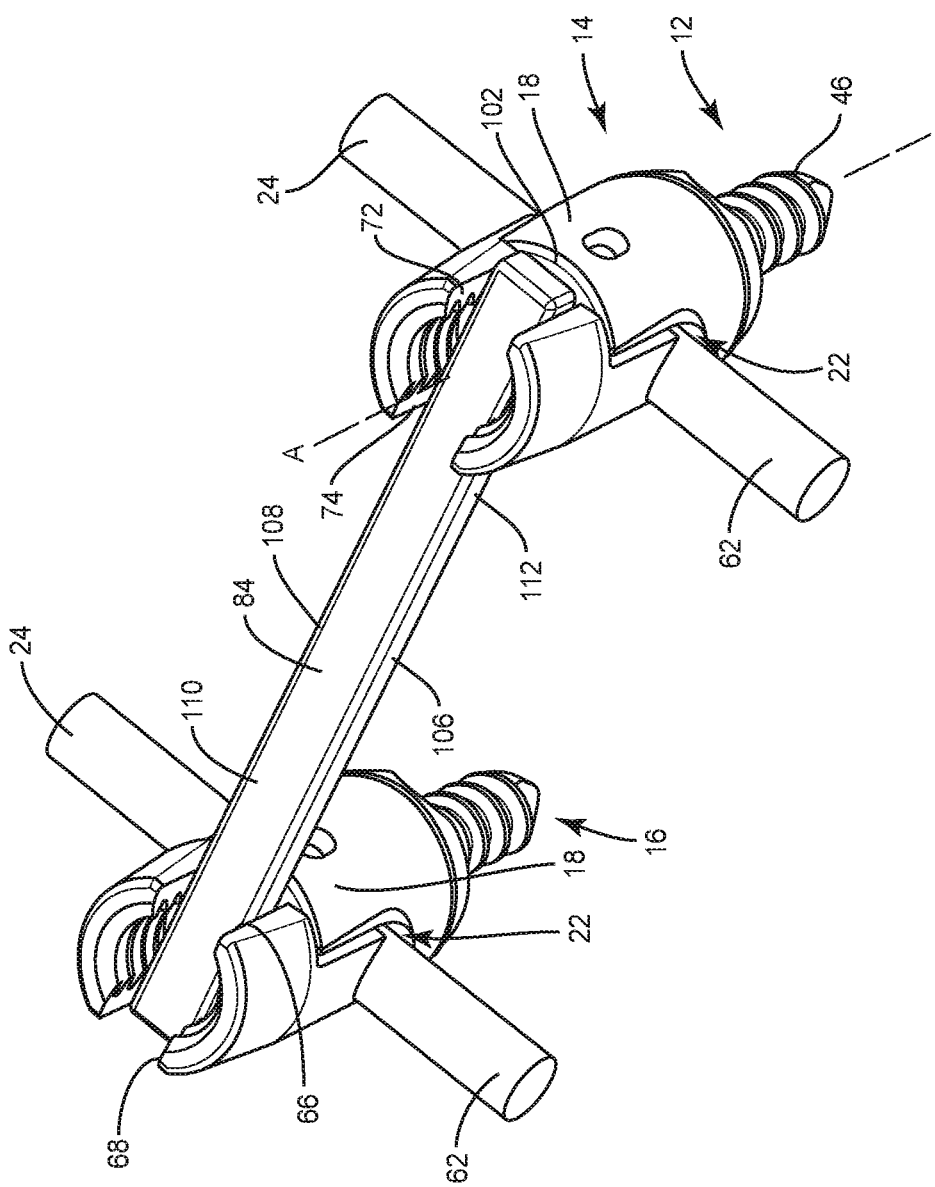
FIG. 6 is a perspective view of components shown in FIG. 1.

Element 84 has a substantially rectangular cross sectional configuration and includes opposite planar side surfaces 106, 108 extending between opposite planar surfaces 110, 112. Surface 106 engages surfaces 66, 68 and surface 108 engages surfaces 72, 74 when element 84 is inserted within passageway 82. Surface 112 engages surfaces 102, 104 when element 84 is inserted within passageway 82, as shown in FIG. 6. In one embodiment, element 84 is disposed to extend along an axial plane, such as, for example, a transverse plane of a body of a patient. In some embodiments, element 84 may have various cross sectional configurations, such as, for example, circular, oval, oblong, triangular, square, polygonal, irregular, uniform, non-uniform, variable, tubular and/or tapered.

Element 84 has a uniform thickness/diameter. In some embodiments, element 84 may have various surface configurations, such as, for example, rough, threaded for connection with surgical instruments, arcuate, undulating, porous, semi-porous, dimpled, polished and/or textured. In some embodiments, the thickness defined by element 84 may be uniformly increasing or decreasing, or have alternate diameter dimensions along its length. In some embodiments, element 84 may have various cross section configurations, such as, for example, oval, oblong, triangular, rectangular, square, polygonal, irregular, uniform, non-uniform, variable and/or tapered. In some embodiments, element 84 may extend in various configurations, such as, for example, linear, arcuate, curved, angular and/or pre-bent according to a selected configuration of vertebrae.

In some embodiments, element 84 may have various lengths. In some embodiments, all or only a portion of element 84 may have a semi-rigid, flexible or elastic configuration and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. In one embodiment, element 84 provides a selective amount of expansion and/or extension in an axial direction. In some embodiments, element 84 may have a flexible configuration, which includes movement in a lateral or side to side direction. In some embodiments, element 84 may be compressible in an axial direction. Element 84 can include a plurality of separately attachable or connectable portions or sections, such as bands or loops, or may be monolithically formed as a single continuous element.

In assembly, operation and use, spinal implant system 10, similar to the systems and methods described herein, is employed with a surgical procedure, as described herein, for treatment of a condition or injury of an affected section of the spine including vertebrae V, as shown in FIG. 7.

In use, to treat the affected section of the spine, a medical practitioner obtains access to a surgical site including vertebrae V in any appropriate manner, such as through incision and retraction of tissues. System 10 may be used in any existing surgical method or technique including open surgery, mini-open surgery, minimally invasive surgery and percutaneous surgical implantation, whereby vertebrae V are accessed through a micro-incision, or sleeve that provides a protected passageway to the area. Once access to the surgical site is obtained, the particular surgical procedure is performed for treating the spinal disorder. System 10 is then employed to augment the surgical treatment System 10 can be delivered or implanted as a pre-assembled device or can be assembled in situ.

Pilot holes are made in vertebrae V1, V2 of vertebrae V along sagittal planes SP1, SP2 of vertebrae V. Fasteners 12, as described herein, are aligned with the pilot holes and fastened with the tissue of vertebrae V1, V2.

Receivers 14 of fasteners 12, disposed with vertebrae V1, V2 along SP1, are selectively rotated relative to shafts 16 to accommodate the orientation of a rod 24A, similar to rod 24 described herein. Rod 24A is positioned in cavities 22 of fasteners 12 such that surface 62 engages surfaces 100 of fasteners 12. In one embodiment, rod 24 is top-loaded into cavities 22. In one embodiment, rod 24 is side-loaded into cavities.

Receivers 14 of fasteners 12, disposed with vertebrae V1, V2 along SP2, are selectively rotated relative to shafts 16 to accommodate the orientation of a rod 24B, similar to rod 24 described herein. Rod 24B is positioned in cavities 22 of fasteners 12 such that surface 62 engages surfaces 100 of fasteners 12.

Figure 4:
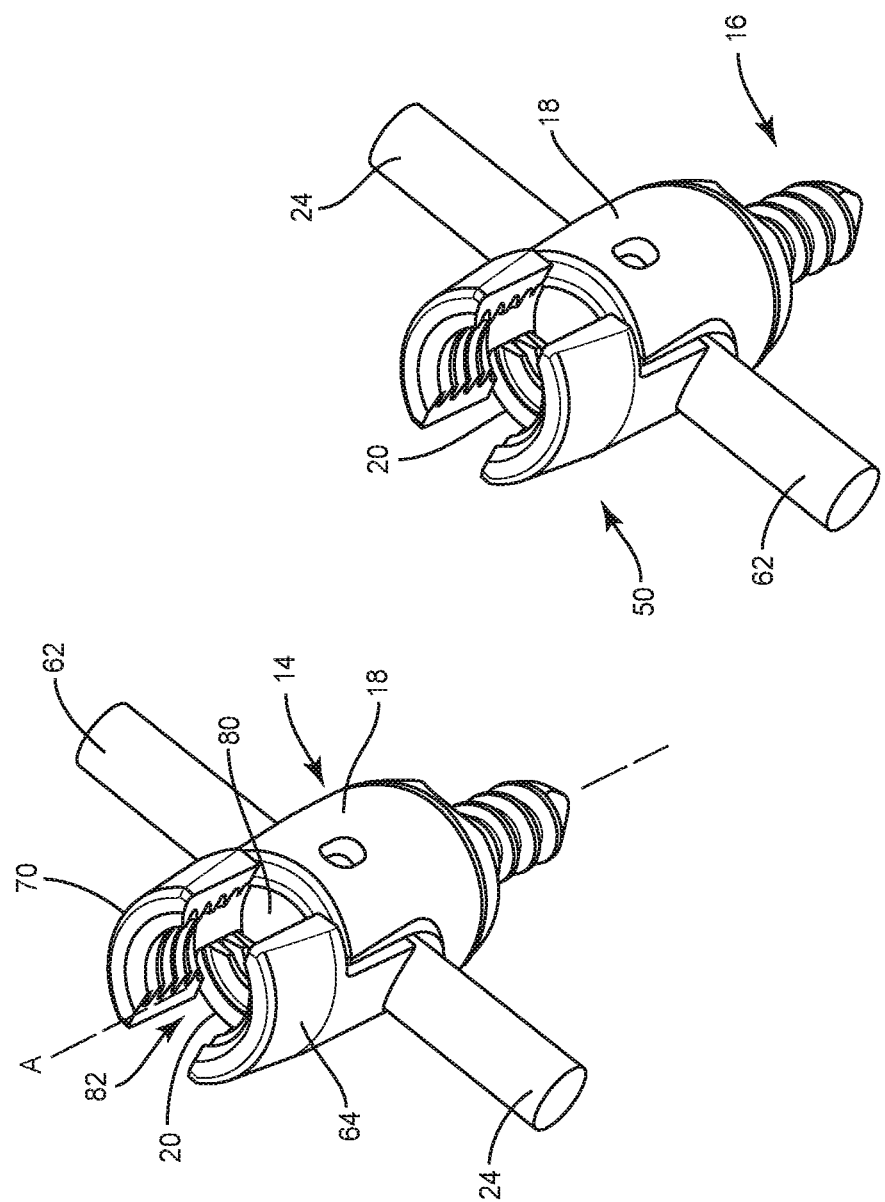
FIG. 4 is a perspective view of components shown in FIG. 1.

Stirrups 50 A-D, similar to stirrup 50 described herein, are positioned relative to receivers 14 of fasteners 12 such that arms 18 are disposed within cavities 96 and arms 20 are disposed within cavities 92, as shown in FIG. 4. When arms 18 are disposed within cavities 96 and arms 20 are disposed within cavities 92, surfaces 30, 32 engage surfaces 56 and surfaces 26, 28 engage surfaces 58, as shown in FIG. 4. Surfaces 60 engage surfaces 62 of rods 24A, 24B. In one embodiment, when arms 18 are disposed within cavities 96 and arms 20 are disposed within cavities 92, surfaces 60 are aligned with surfaces 100 such that surfaces 60, 100 are continuous with one another and define a channel having a cylindrical cross sectional configuration that conforms to that of rod 24.

Figure 5:
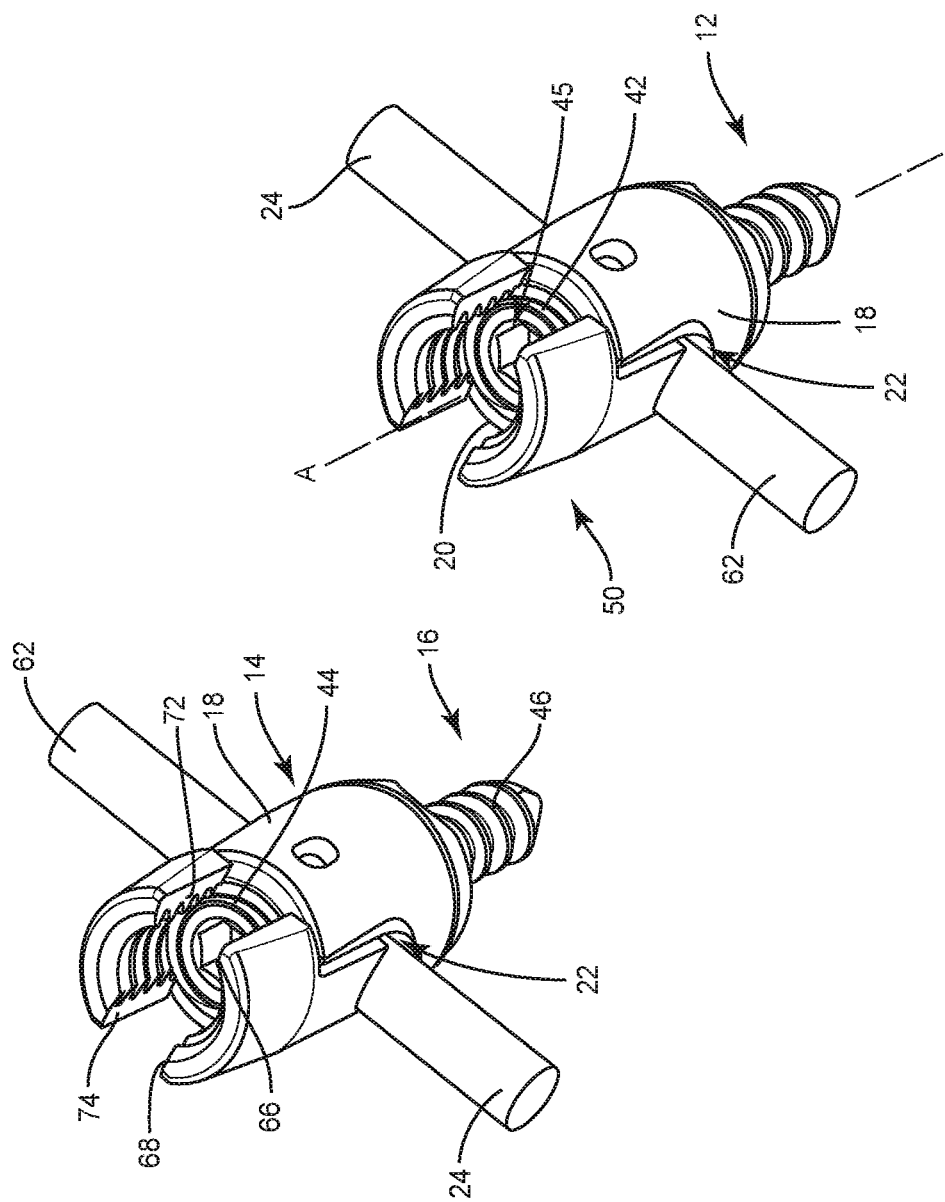
FIG. 5 is a perspective view of components shown in FIG. 1.

Setscrews 44, as described herein, are positioned between extensions 64, 70 of stirrups 50 such that the thread forms on surfaces 76, 78 of extensions 64, 70 are aligned with the threads on surfaces 42. Setscrews 44 are rotated about axis A in a first direction, such as, for example, clockwise or counterclockwise, such that the thread forms on surfaces 76, 78 engage the thread forms on surfaces 42, causing setscrews 44 to move distally relative to stirrups 50. Setscrews 44 are translated distally until the thread forms on surfaces 38, 40 are aligned with the thread form on surfaces 42. Setscrews 44 are rotated about axis A in a first direction, such as, for example, clockwise or counterclockwise, such that the thread forms on surfaces 38, 40 engage the thread forms on surfaces 42, causing setscrews 44 to move distally relative to receivers 14, as shown in FIG. 5. Setscrews 44 are rotated in the first direction until distal end surfaces of setscrews 44 engage surfaces 80. In some embodiments, this configuration fixes stirrups 50 relative to fasteners 12. In one embodiment, a tip of a tool, such as, for example a driver is inserted into openings 45 and the tool is used to rotate setscrews 44 about axis A to fix setscrews 44 relative to receivers 14. In one embodiment, proximal end surfaces of setscrews 44 are flush with surfaces 102, 104 when the distal end surfaces of setscrews 44 engage surfaces 80. In one embodiment, inner surfaces of members opposite surfaces 56, 58 are threaded. In some embodiments, the threads on the inner surfaces of stirrups 50 opposite surfaces 56, 58 are continuous with threads on surfaces 38, 40 of fasteners 12 to allow setscrews 44 to be rotated about axis A in a first direction, such as, for example, clockwise or counterclockwise, such that the thread forms on surfaces 38, 40 and the thread form on the inner surfaces of stirrups 50 opposite surfaces 56, 58 engage the thread form on surfaces 42, causing setscrews 44 to move distally relative to receivers 14.

Elements 84, as described herein, are positioned within passageways 82 such that surfaces 112 engages surfaces 102, 104, surfaces 106 engage surfaces 66, 68 and surfaces 108 engages surfaces 72, 74, as shown in FIG. 6.

Set screws 88 A-D, similar to set screws 88 described herein, are positioned between extensions 64, 70 of stirrups 50 such that the thread forms on surfaces 76, 78 are aligned with the thread forms on surfaces 86. Set screws 88 are rotated about axis A in a first direction, such as, for example, clockwise or counterclockwise, such that the thread forms on surfaces 76, 78 engage the thread forms on surfaces 86, causing set screws 88 to move distally relative to stirrups 50, as shown in FIGS. 1 and 7. Set screws 88 are rotated in the first direction until distal end surfaces of set screws 88 engage surfaces 110 of element 84. When the thread forms on surfaces 76, 78 of stirrups 50 engage the thread forms on surfaces 86, element 84 is positioned between set screws 88 and surfaces 80. In one embodiment, a tip of a tool, such as, for example a driver is inserted into openings 90 of set screws 88 and the tool is used to rotate set screws 88 about axis A to fix set screws 88 relative to stirrups 50. In one embodiment, proximal end surfaces of set screws 88 are flush with surfaces 114, 116 when the distal end surfaces of set screws 88 engage surfaces 110.

Upon completion of the procedure, the surgical instruments, assemblies and non-implanted components of spinal implant system 10 are removed and the incision is closed. Spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes one or more fasteners, not shown, for attaching a spinal construct with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 8:
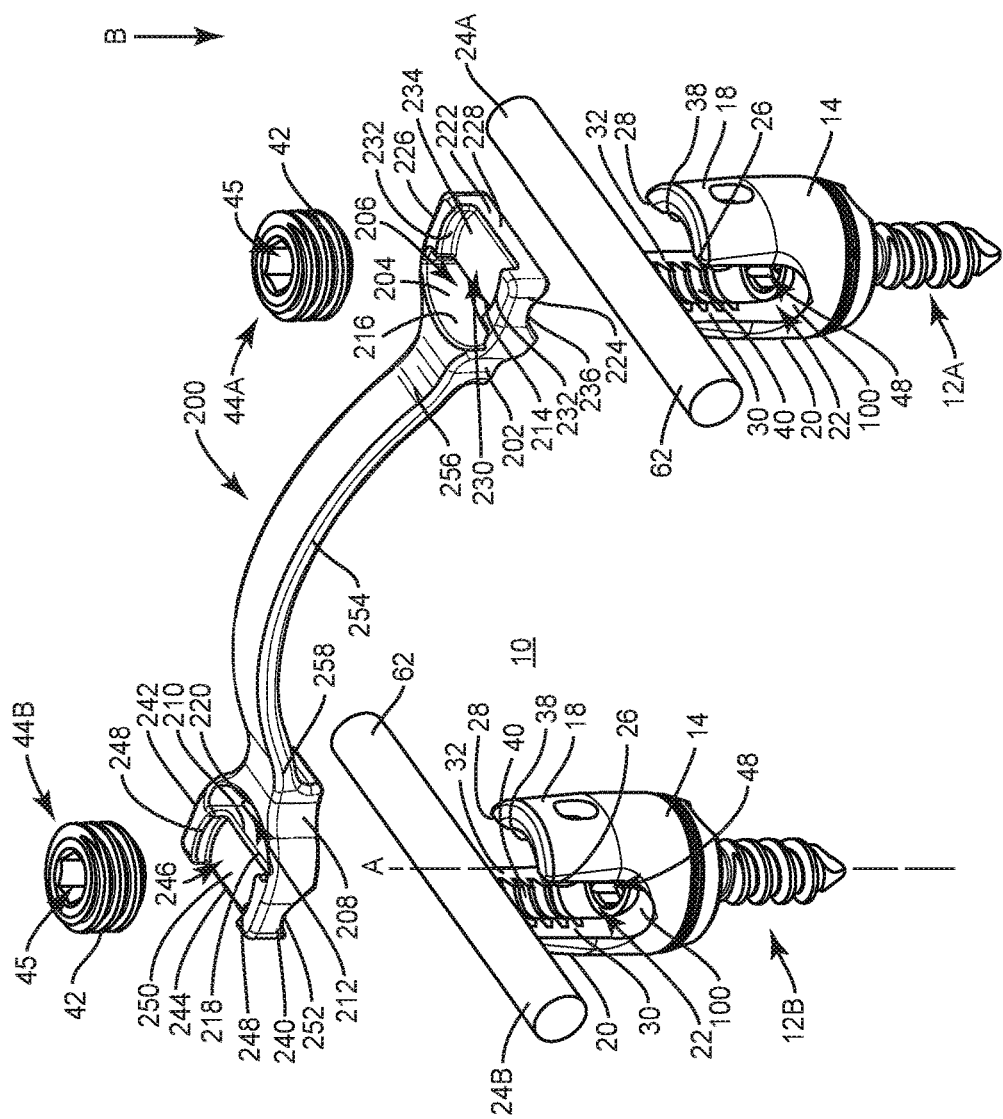
FIG. 8 is a perspective view of components of one embodiment of a system in accordance with the principles of the present disclosure.

In one embodiment, as shown in FIG. 8, system 10, similar to the systems and methods described with regard to FIGS. 1-7, includes a spinal construct comprising fasteners 12A, 12B, similar to fastener 12 described herein, and rods 24A, 24B, similar to rod 24 described herein. A connecting element 200, similar to element 84 described herein, extends between a member, such as, for example, an end stirrup 202 including an inner surface 204 defining a cavity 206 configured for disposal of arm 18 or arm 20 of fastener 12A such that surface 204 matingly engages arm 18 or arm 20. Element 200 includes a member, such as, for example, an end stirrup 208 opposite end stirrup 202 that includes an inner surface 210 defining a cavity 212 configured for disposal of arm 18 or arm 20 of fastener 12B.

Cavity 206 is defined by planar surface 214 and an arcuate surface 216 that faces surface 214 such that cavity 206 has a hemispherical configuration. Cavity 212 is defined by planar surface 218 that faces opposite surface 216 and an arcuate surface 220 that faces surface 218 such that cavity 212 has a hemispherical configuration.

End 202 includes a bridge 222 extending between an end 224 and an end 226. Bridge 222 has a width defined by the distance between surface 214 and an opposite planar end surface 228. Bridge includes a recess 230 defined by arcuate side surfaces 232 that face one another and a planar upper surface 234 of end stirrup 202 that faces opposite an implant engaging surface 236 of end stirrup 202. Surface 236 is concavely curved between surfaces 214, 228 and is configured to engage surface 62 of rod 24A when rod 24A is disposed in cavity 22 of fastener 12A to fix rod 24A relative to receiver 14 of fastener 12A.

End stirrup 208 includes a bridge 238 extending between an end 240 and an end 242. Bridge 238 has a width defined by the distance between surface 218 and an opposite planar end surface 244. Bridge 238 includes a recess 246 defined arcuate side surfaces 248 that face one another. Recess 246 includes a planar upper surface 250 opposite an implant engaging surface 252 of end stirrup 208. Surface 252 is concavely curved between surfaces 218, 244 and is configured to engage surface 62 of rod 24B when rod 24B is disposed in cavity 22 of fastener 12B to fix rod 24B relative to receiver 14 of fastener 12B.

Element 200 includes a connecting portion 254 that spans between end stirrups 202, 208. Portion 254 has an arcuate configuration between ends 256, 258 of portion 254. In some embodiments, portion 254 has a continuous radius of curvature between ends 256, 258. In some embodiments, ends 202, 256 and ends 208, 258 are integrally formed with one another such that portion 254 and end stirrups 202, 208 are monolithic.

Receiver 14 of fastener 12A is selectively rotated relative to shaft 16 of fastener 12A to accommodate the orientation of rod 24A such that rod 24A is aligned with cavity 22 of fastener 12A. Rod 24A is positioned in cavity 22 of fastener 12A such that surface 62 of rod 24A engages surface 100 of fastener 12A.

Receiver 14 of fastener 12B is selectively rotated relative to shaft 16 of fastener 12B to accommodate the orientation of rod 24B such that rod 24B is aligned with cavity 22 of fastener 12B. Rod 24B is positioned in cavity 22 of fastener 12B such that surface 62 of rod 24B engages surface 100 of fastener 12B.

End stirrup 202 is connected to fastener 12A by disposing arm 20 of fastener 12A in cavity 206 such that surface 36 of fastener 12A engages surface 216 and surface 214 engages surfaces 30, 32 of fastener 12A. A setscrew 44A, similar to setscrew 44 described herein, is positioned in recess 230 such that the threads on surface 42 of setscrew 44A are aligned with the threads on surfaces 38, 40 of fastener 12A.

Setscrew 44A is rotated about axis A in a first direction, such as, for example, clockwise or counterclockwise, such that the thread forms on surfaces 38, 40 of fastener 12A engage the thread form on surface 42 of member 42A, causing setscrew 44A to move distally relative to receiver 14 of fastener 12A, as shown by arrow B in FIG. 8. As setscrew 44A translates, in the direction shown by arrow B, a lower surface of setscrew 44A engages surface 234 such that translating setscrew 44A, in the direction shown by arrow B, also causes end 202 to translate relative to fastener 12A, in the direction shown by arrow B. Setscrew 44A is rotated in the first direction until surface 236 engages surface 62 or rod 24A to fix rod 24A relative to receiver 14 of fastener 12A.

End 208 is connected to fastener 12B by disposing arm 18 of fastener 12B in cavity 212 such that surface 34 of fastener 12B engages surface 220 and surface 218 engages surfaces 26, 28 of fastener 12B. A setscrew 44B, similar to setscrew 44, is positioned in recess 246 such that the threads on surface 42 of setscrew 44B are aligned with the threads on surfaces 38, 40 of fastener 12B.

Setscrew 44B is rotated about axis A in the first direction, such as, for example, clockwise or counterclockwise, such that the thread forms on surfaces 38, 40 of fastener 12B engage the thread form on surface 42 of setscrew 44B, causing setscrew 44B to move distally relative to receiver 14 of fastener 12B, as shown by arrow B in FIG. 8. As setscrew 44B translates, in the direction shown by arrow B, a lower end surface of setscrew 44B engages surface 250 such that translating setscrew 44B, in the direction shown by arrow B, also causes end 208 to translate relative to fastener 12B, in the direction shown by arrow B. Setscrew 44B is rotated in the first direction until surface 252 engages surface 62 of rod 24B to fix rod 24B relative to receiver 14 of fastener 12B.

Figure 9:
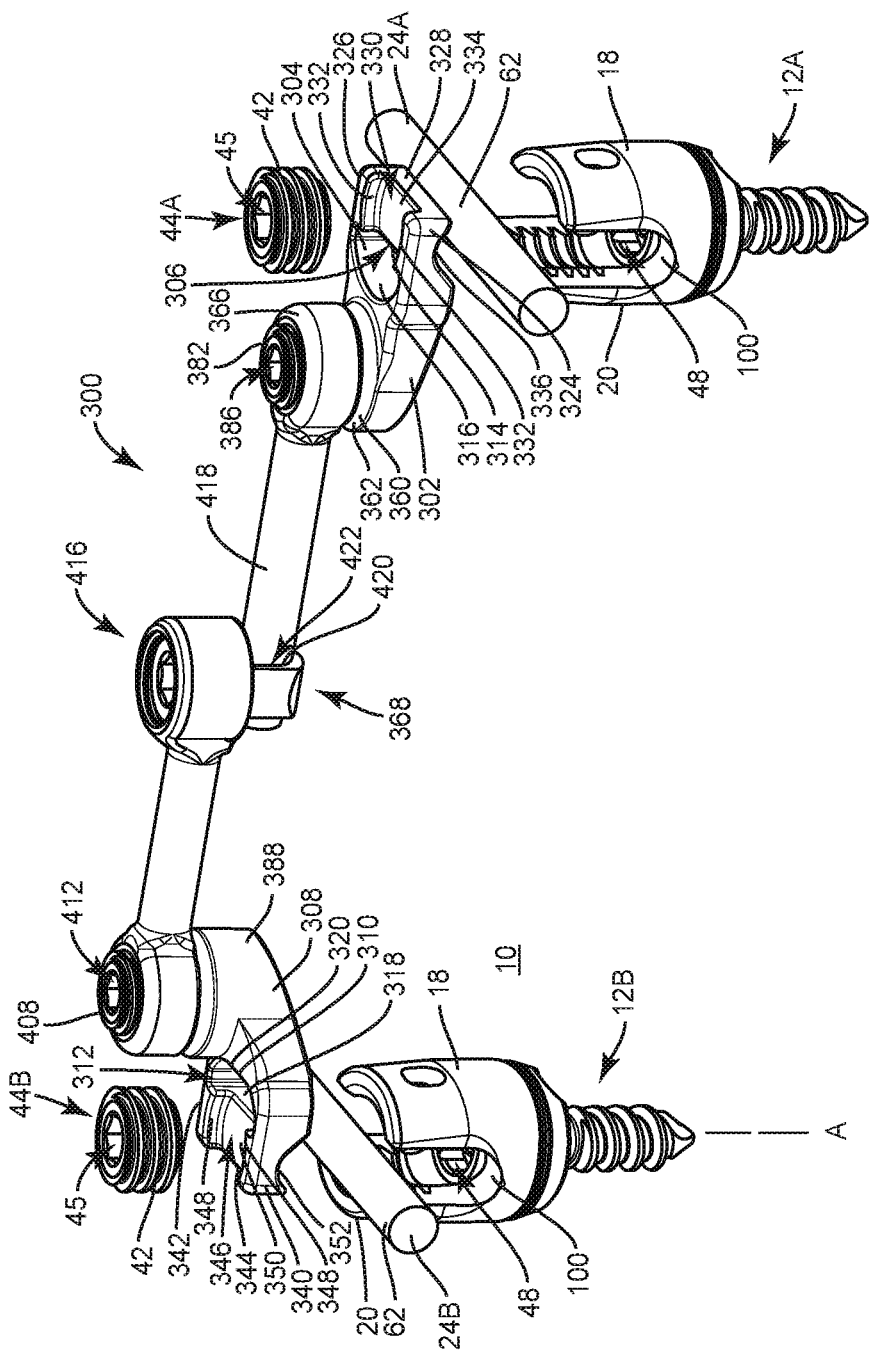
FIG. 9 is a perspective view of components of one embodiment of a system in accordance with the principles of the present disclosure.
Figure 10:
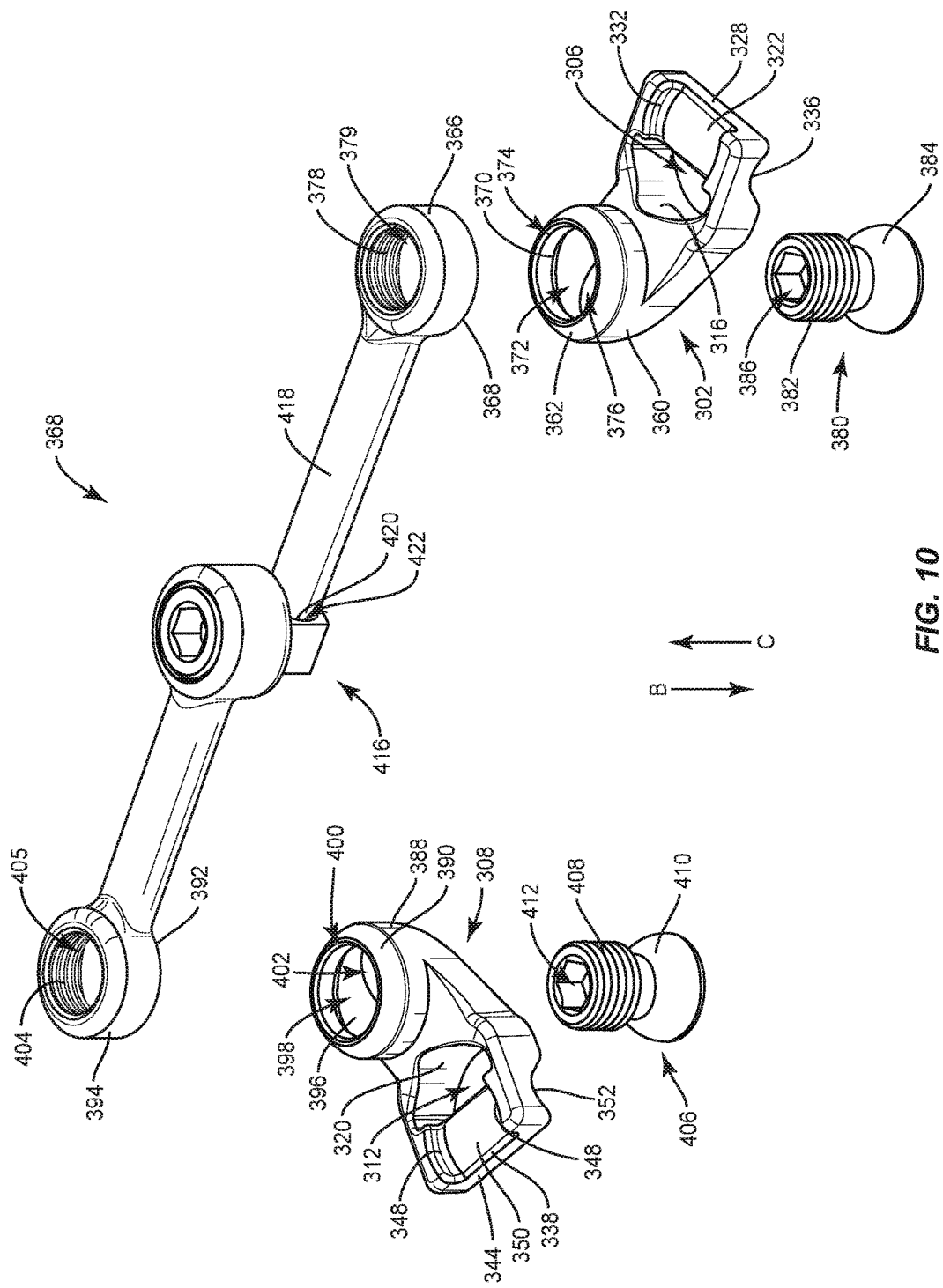
FIG. 10 is a perspective view of components shown in FIG. 9.

In one embodiment, as shown in FIGS. 9 and 10, system 10, similar to the systems and methods described herein, includes a spinal construct comprising fasteners 12A, 12B and rods 24A, 24B. A connecting element 300, similar to element 84 described herein, extends between an end stirrup 302, similar to end stirrup 202 described herein, and an opposite end stirrup 308, similar to end stirrup 208. End stirrup 302 includes an inner surface 304 defining a cavity 306 configured for disposal of arm 18 or arm 20 of fastener 12A such that surface 304 matingly engages arm 18 or arm 20 of fastener 12A. End stirrup 308 includes an inner surface 310 defining a cavity 312 configured for disposal of an arm 18 or an arm 20 of fastener 12B such that surface 310 matingly engages arm 18 or arm 20 of fastener 12B.

Cavity 306 is defined by a planar surface 314 and an arcuate surface 316 that faces surface 314 such that cavity 306 has a hemispherical configuration. Cavity 312 is defined by a planar surface 318 that faces opposite surface 316 and an arcuate surface 320 that faces surface 318 such that cavity 312 has a hemispherical configuration.

End stirrup 302 includes a bridge 322 extending between an end 324 and an end 326. Bridge 322 has a width defined by the distance between surface 314 and an opposite planar end surface 328. Bridge 322 includes a recess 330 defined by arcuate side surfaces 332 that face one another and a planar upper surface 334 of end stirrup 302 that faces opposite an implant engaging surface 336 of end stirrup 302. Surface 336 is concavely curved between surfaces 314, 328 and is configured to engage surface 62 of rod 24A when rod 24A is disposed in cavity 22 of fastener 12A to fix rod 24A relative to receiver 14 of fastener 12A.

End stirrup 302 includes a connecting portion 360 opposite bridge 322. Portion 360 includes a tapered upper surface 362 configured to engage a tapered bottom surface 364 of an end 366 of a linkage, such as, for example, a connecting portion 368. Portion 360 includes an unthreaded inner surface 370 defining a channel 372 having openings 374, 376 at top and bottom ends of portion 360, respectively. End 366 includes a threaded inner surface 378 defining a passageway 379. In some embodiments, end 366 is separate from end stirrup 302 and is attachable to end stirrup 302. In some embodiments, end 366 is monolithically formed with end stirrup 302.

To rotatably fix end 366 with portion 360, a coupling member 380 having an end 382 with a threaded outer surface and an end 384 with an unthreaded outer surface is bottom-loaded into channel 372 such that end 382 translates, in the direction shown by arrow C, through opening 376 toward opening 374. Member 380 is translated, in the direction shown by arrow C, until the threads on the outer surface of end 382 are aligned with the threads on surface 378. Member 380 is rotated in a first direction, such as, for example, clockwise or counterclockwise, such that the threads on the outer surface of end 382 engage the threads on surface 378. As the threads on the outer surface of end 382 engage the threads on surface 378, member 380 translates relative to end 366, in the direction shown by arrow C, into passageway 379. Member 380 is translated relative to end 366, in the direction shown by arrow C, until the outer surface of end 384 engages a bottom end surface of portion 360. In one embodiment, a tip of a tool, such as, for example a driver is inserted into an opening 386 in end 382 and the tool is used to rotate member 380 about axis A to rotatably fix end 302 relative to portion 368. In some embodiments, end stirrup 302 can be variously connected with portion 368, such as, for example, monolithic, integral connection, frictional engagement, threaded engagement, mutual grooves, screws, adhesive, nails, barbs and/or raised element.

End stirrup 308 includes a bridge 338 extending between an end 340 and an end 342. Bridge 338 has a width defined by the distance between surface 318 and an opposite planar end surface 344. Bridge 338 includes a recess 346 defined by arcuate side surfaces 348 that face one another. Recess 346 includes a planar upper surface 350 opposite an implant engaging surface 352 of end stirrup 308. Surface 352 is concavely curved between surfaces 318, 344 and is configured to engage surface 62 of rod 24B when rod 24B is disposed in cavity 22 of fastener 12B to fix rod 24B relative to receiver 14 of fastener 12B.

End stirrup 308 includes a connecting portion 388 opposite bridge 338. Portion 388 includes a tapered upper surface 390 configured to engage a tapered bottom surface 392 of a second end 394 of portion 368. Portion 388 includes an unthreaded inner surface 396 defining a channel 398 having openings 400, 402 at top and bottom ends of portion 388, respectively. End 394 includes a threaded inner surface 404 defining a passageway 405. In some embodiments, end 394 is separate from end stirrup 308 and is attachable to end stirrup 308. In some embodiments, end 394 is monolithically formed with end stirrup 308.

To rotatably fix end 394 with portion 388, a coupling member 406 having an end 408 with a threaded outer surface and an end 410 with an unthreaded outer surface is bottom-loaded into channel 398 such that end 408 translates, in the direction shown by arrow C, through opening 402 toward opening 400. Member 406 is translated, in the direction shown by arrow C, until the threads on the outer surface of end 408 are aligned the threads on surface 404. Member 406 is rotated in a first direction, such as, for example, clockwise or counterclockwise, such that the threads on the outer surface of end 408 engage the threads on surface 404. As the threads on the outer surface of end 408 engage the threads on surface 404, member 406 translates relative to end 394, in the direction shown by arrow C, into passageway 405. Member 406 is translated relative to end 394, in the direction shown by arrow C, until the outer surface of end 410 engages a bottom end surface of portion 388.

Portion 368 spans between ends 366, 394 and includes an intermediate portion 416 that connects end 366 with end 394 such that end 366 is rotatable relative to end 394. In some embodiments, end 366 includes a shaft 418 and end 394 includes a body having an inner surface 420 defining a through hole 422 configured for slidable disposal of shaft 418 to allow the length of portion 368 to be adjusted, depending upon, for example, the distance between fasteners 12A, 12B.

Receiver 14 of fastener 12A is selectively rotated relative to shaft 16 of fastener 12A to accommodate the orientation of rod 24A such that rod 24A is aligned with cavity 22 of fastener 12A. Rod 24A is positioned in cavity 22 of fastener 12A such that surface 62 of rod 24A engages surface 100 of fastener 12A. Receiver 14 of fastener 12B is selectively rotated relative to shaft 16 of fastener 12B to accommodate the orientation of rod 24B such that rod 24B is aligned with cavity 22 of fastener 12B. Rod 24B is positioned in cavity 22 of fastener 12B such that surface 62 of rod 24B engages surface 100 of fastener 12B. Rod 24A is in alignment with axis A when rod 24A is disposed in cavity 22 of fastener 12A such that axis A intersects or extends through rod 24A. Rod 24B is in alignment with axis A when rod 24B is disposed in cavity 22 of fastener 12B such that axis A intersects or extends through rod 24B.

End stirrup 302 is connected to fastener 12A by disposing arm 20 of fastener 12A in cavity 306 such that surface 36 of fastener 12A engages surface 316 and surface 314 engages surfaces 30, 32 of fastener 12A A setscrew 44A is positioned in recess 330 such that the threads on surface 42 of setscrew 44A are aligned with the threads on surfaces 38, 40 of fastener 12A. Setscrew 44A is rotated about axis A in a first direction, such as, for example, clockwise or counterclockwise, such that the thread forms on surfaces 38, 40 of fastener 12A engage the thread form on surface 42 of setscrew 44A, causing setscrew 44A to move distally relative to receiver 14 of fastener 12A, as shown by arrow B in FIG. 9. As setscrew 44A translates, in the direction shown by arrow B, a lower surface of setscrew 44A engages surface 334 such that translating setscrew 44A, in the direction shown by arrow B, also causes end stirrup 302 to translate relative to fastener 12A, in the direction shown by arrow B. Setscrew 44A is rotated in the first direction until surface 336 engages surface 62 of rod 24A to fix rod 24A relative to receiver 14 of fastener 12A.

End 366 is rotatably fixed with portion 360 by bottom-loading member 380 into channel 372 such that end 382 translates, in the direction shown by arrow C, through opening 376 toward opening 374. Member 380 is translated, in the direction shown by arrow C, until the threads on the outer surface of end 382 are aligned with the threads on surface 378. Member 380 is rotated in a first direction, such as, for example, clockwise or counterclockwise, such that the threads on the outer surface of end 382 engage the threads on surface 378. As the threads on the outer surface of end 382 engage the threads on surface 378, member 380 translates relative to end 366, in the direction shown by arrow C, into passageway 379. Member 380 is translated relative to end 366, in the direction shown by arrow C, until the outer surface of end 384 engages a bottom end surface of portion 360.

End 308 is connected to fastener 12B by disposing arm 18 of fastener 12B in cavity 312 such that surface 34 of fastener 12B engages surface 320 and surface 318 engages surfaces 26, 28 of fastener 12B. A setscrew 44B is positioned in recess 346 such that the threads on surface 42 of setscrew 44B are aligned with the threads on surfaces 38, 40 of fastener 12B. Setscrew 44B is rotated about axis A in a first direction, such as, for example, clockwise or counterclockwise, such that the thread forms on surfaces 38, 40 of fastener 12B engage the thread form on surface 42 of setscrew 44B, causing setscrew 44B to move distally relative to receiver 14 of fastener 12B, as shown by arrow B in FIG. 10. As setscrew 44B translates, in the direction shown by arrow B, a lower end surface of setscrew 44B engages surface 350 such that translating setscrew 44B, in the direction shown by arrow B, also causes end 308 to translate relative to fastener 12B, in the direction shown by arrow B. Setscrew 44B is rotated in the first direction until surface 352 engages surface 62 of rod 24B to fix rod 24B relative to receiver 14 of fastener 12B.

End 394 is rotatably fixed with portion 388 by bottom-loading member 406 into channel 398 such that end 408 translates, in the direction shown by arrow C, through opening 402 toward opening 400. Member 406 is translated, in the direction shown by arrow C, until the threads on the outer surface of end 408 are aligned the threads on surface 404. Member 406 is rotated in a first direction, such as, for example, clockwise or counterclockwise, such that the threads on the outer surface of end 408 engage the threads on surface 404. As the threads on the outer surface of end 408 engage the threads on surface 404, member 406 translates relative to end 394, in the direction shown by arrow C, into passageway 405. Member 406 is translated relative to end 394, in the direction shown by arrow C, until the outer surface of end 410 engages a bottom end surface of portion 388. End stirrup 302 may be rotated relative to end stirrup 308 about portion 416 to adjust the position of end stirrup 302 relative to end stirrup 308.

Figure 11:
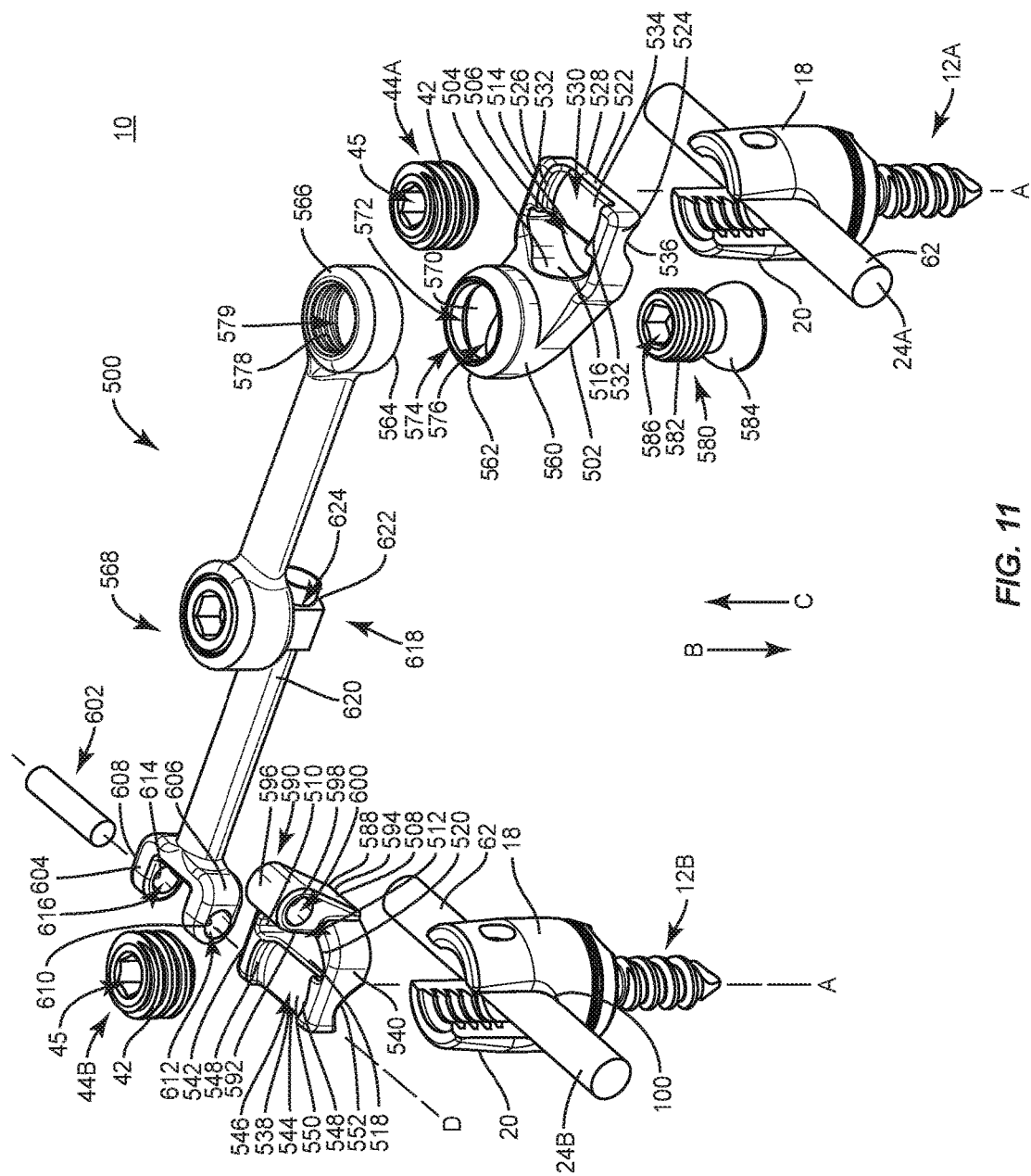
FIG. 11 is a perspective view of components of one embodiment of a system in accordance with the principles of the present disclosure.

In one embodiment, as shown in FIG. 11, system 10, similar to the systems and methods described herein, includes a spinal construct comprising fasteners 12A, 12B and rods 24A, 24B. A connecting element 500 extends between an end stirrup 502, similar to those described herein, and an opposite end stirrup 508. End stirrup 502 includes an inner surface 504 defining a cavity 506 configured for disposal of arm 18 or arm 20 of fastener 12A such that surface 504 matingly engages arm 18 or arm 20 of fastener 12A. End stirrup 508 includes an inner surface 510 defining a cavity 512 configured for disposal of an arm 18 or an arm 20 of fastener 12B such that surface 510 matingly engages arm 18 or arm 20 of fastener 20.

Cavity 506 is defined by a planar surface 514 and an arcuate surface 516 that faces surface 514 such that cavity 506 has a hemispherical configuration. Cavity 512 is defined by a planar surface 518 that faces opposite surface 516 and an arcuate surface 520 that faces surface 518 such that cavity 512 has a hemispherical configuration.

End stirrup 502 includes a bridge 522 extending between an end 524 and an end 526. Bridge 522 has a width defined by the distance between surface 514 and an opposite planar end surface 528. Bridge 522 includes a recess 530 defined by arcuate side surfaces 532 that face one another and a planar upper surface 534 of end stirrup 502 that faces opposite an implant engaging surface 536 of end stirrup 502. Surface 536 is concavely curved between surfaces 514, 528 and is configured to engage surface 62 of rod 24A when rod 24A is disposed in cavity 22 of fastener 12A to fix rod 24A relative to receiver 14 of fastener 12A.

End stirrup 502 includes a connecting portion 560 opposite bridge 522. Portion 560 includes a tapered upper surface 562 configured to engage a tapered bottom surface 564 of an end 566 of a linkage, such as, for example, a connecting portion 568. Portion 560 includes an unthreaded inner surface 570 defining a channel 572 having openings 574, 576 at top and bottom ends of portion 560, respectively. End 566 includes a threaded inner surface 578 defining a passageway 579.

To rotatably fix end 566 with portion 560, a coupling member 580, similar to member 380 described herein, has an end 582 with a threaded outer surface and an end 584 with an unthreaded outer surface is bottom-loaded into channel 572 such that end 582 translates, in the direction shown by arrow C, through opening 576 toward opening 574. Member 580 is translated, in the direction shown by arrow C, until the threads on the outer surface of end 582 are aligned with the threads on surface 578. Member 580 is rotated in a first direction, such as, for example, clockwise or counterclockwise, such that the threads on the outer surface of end 582 engage the threads on surface 578. As the threads on the outer surface of end 582 engage the threads on surface 578, member 580 translates relative to end 566, in the direction shown by arrow C, into passageway 579. Member 580 is translated relative to end 566, in the direction shown by arrow C, until the outer surface of end 584 engages a bottom end surface of portion 560.

End 508 includes a bridge 538 extending between an end 540 and an end 542. Bridge 538 has a width defined by the distance between surface 518 and an opposite planar end surface 544. Bridge 538 includes a recess 546 defined by arcuate side surfaces 548 that face one another. Recess 546 includes a planar upper surface 550 opposite an implant engaging surface 552 of end 508. Surface 552 is concavely curved between surfaces 518, 544 and is configured to engage surface 62 of rod 24B when rod 24B is disposed in cavity 22 of fastener 12B to fix rod 24B relative to receiver 14 of fastener 12B.

End 508 includes a connecting portion 588 opposite bridge 538. Portion 588 includes an extension 590 including a planar surface 592 extending parallel to axis A and/or surface 550 and a planar surface 594 extending at an acute angle relative to axis A and/or surface 550. Extension 590 includes an arcuate surface 596 extending between surfaces 592, 594. Extension 590 includes an inner surface 598 defining an aperture 600 having a cylindrical cross-sectional configuration that extends perpendicular to axis A Aperture 600 is configured for removable disposal of a pin 602 to rotatably fix an end 604 of portion 568 relative to end 508. In some embodiments, surface 592, surface 594 and/or aperture 600 may be disposed at alternate orientations, relative to axis A such as, for example, parallel, transverse, perpendicular and/or other angular orientations such as acute or obtuse, co-axial and/or may be offset or staggered. In some embodiments, all or only a portion of surface 592, surface 594, surface 596 and/or surface 598 may be variously configured and dimensioned, such as, for example, planar, concave, convex, polygonal, irregular, uniform, non-uniform, staggered, tapered, consistent or variable. In some embodiments, surface 598 may have various surface configurations, such as, for example, smooth and/or surface configurations to enhance fixation with pin 602, such as, for example, rough, arcuate, undulating, porous, semi-porous, dimpled, polished and/or textured. In some embodiments, aperture 600 may have various cross section configurations, such as, for example, oval, oblong, triangular, rectangular, square, polygonal, irregular, uniform, non-uniform, variable, tubular and/or tapered.

End 604 includes a pair of spaced apart arms 606, 608 such that extension 590 may be positioned between arms 606, 608. Arm 606 includes an inner surface 610 defining a cavity 612 having a cylindrical cross-sectional configuration and extending perpendicular to axis A and parallel to aperture 600. Arm 606 includes an inner surface 614 defining a cavity 616 having a cylindrical cross-sectional configuration and extending perpendicular to axis A and parallel to aperture 600. Cavity 612 is aligned with cavity 616. In some embodiments, cavity 612 and/or cavity 616 may be disposed at alternate orientations, relative to axis A, such as, for example, parallel, transverse, perpendicular and/or other angular orientations such as acute or obtuse, co-axial and/or may be offset or staggered. In some embodiments, surface 610 and/or surface 614 may have various surface configurations, such as, for example, smooth and/or surface configurations to enhance fixation with pin 602, such as, for example, rough, arcuate, undulating, porous, semi-porous, dimpled, polished and/or textured. In some embodiments, cavity 612 and/or cavity 616 may have various cross section configurations, such as, for example, oval, oblong, triangular, rectangular, square, polygonal, irregular, uniform, non-uniform, variable, tubular and/or tapered. In some embodiments, at least one end of pin 602 is beveled to facilitate insertion of pin 602 into cavity 612 and/or cavity 616.

To rotatably fix end 606 with extension 590, end 606 is positioned relative to extension 590 such that aperture 600 and cavities 612, 616 are aligned or coaxial. Pin 602 is then inserted into cavity 616 and is translated toward cavity 612. Pin 602 is translated toward cavity 612 until at least a portion of pin 602 is positioned within cavity 612. This configuration allows end 508 to rotate or pivot relative to end 606 about an axis D defined by cavities 612, 616. In one embodiment, pin 602 is inserted into cavity 612 and is translated toward cavity 616. Pin 602 is translated toward cavity 616 until at least a portion of pin 602 is positioned within cavity 616. In some embodiments aperture 600 has a first diameter that is greater than second diameters of cavities 612, 616 and pin 602 has a third diameter that is less than the first diameter and slightly less than or equal to the second diameter such that pin 602 forms a friction fit with cavities 612,616, while still allowing extension 590 to pivot about axis D. In some embodiments, end 508 can be variously connected with end 606, such as, for example, monolithic, integral connection, frictional engagement, threaded engagement, mutual grooves, screws, adhesive, nails, barbs and/or raised element.

Portion 568 spans between ends 566, 606 and includes an intermediate portion 618 that connects end 566 with end 606 such that end 566 is rotatable to end 606. In some embodiments, end 606 includes a shaft 620 and end 564 includes a body having an inner surface 622 defining a through hole 624 configured for slidable disposal of shaft 620 to allow the length of portion 568 to be adjusted, depending upon, for example, the distance between fasteners 12A, 12B.

Receiver 14 of fastener 12A is selectively rotated relative to shaft 16 of fastener 12A to accommodate the orientation of rod 24A such that cavity 22 of fastener 12A is aligned with rod 24A. Rod 24A is positioned in cavity 22 of fastener 12A such that surface 62 of rod 24A engages surface 100 of fastener 12A. Receiver 14 of fastener 12B is selectively rotated relative to shaft 16 of fastener 12B to accommodate the orientation of rod 24B such that cavity 22 of fastener 12B is aligned with rod 24B. Rod 24B is positioned in cavity 22 of fastener 12B such that surface 62 of rod 24B engages surface 100 of fastener 12B. Rod 24A is in alignment with axis A when rod 24A is disposed in cavity 22 of fastener 12A such that axis A intersects or extends through rod 24A. Rod 24B is in alignment with axis A when rod 24B is disposed in cavity 22 of fastener 12B such that axis A intersects or extends through rod 24B.

End stirrup 502 is connected to fastener 12A by disposing arm 20 of fastener 12A in cavity 506 such that surface 36 of fastener 12A engages surface 516 and surface 514 engages surfaces 30, 32 of fastener 12A. A setscrew 44A is positioned in recess 530 such that the threads on surface 42 of setscrew 44A are aligned with the threads on surfaces 38, 40 of fastener 12A.

Setscrew 44A is rotated about axis A in a first direction, such as, for example, clockwise or counterclockwise, such that the thread forms on surfaces 38, 40 of fastener 12A engage the thread form on surface 42 of setscrew 44A, causing setscrew 44A to move distally relative to receiver 14 of fastener 12A, as shown by arrow B in FIG. 11. As setscrew 44A translates, in the direction shown by arrow B, a lower surface of setscrew 44A engages surface 534 such that translating setscrew 44A, in the direction shown by arrow B also causes end 502 to translate relative to fastener 12A, in the direction shown by arrow B. Setscrew 44A is rotated in the first direction until surface 536 engages surface 62 of rod 24A to fix rod 24A relative to receiver 14 of fastener 12A.

End 566 is rotatably fixed with portion 560 by bottom-loading member 580 into channel 572 such that end 582 translates, in the direction shown by arrow C, through opening 576 toward opening 574. Member 580 is translated, in the direction shown by arrow C, until the threads on the outer surface of end 582 are aligned with the threads on surface 578. Member 580 is rotated in a first direction, such as, for example, clockwise or counterclockwise, such that the threads on the outer surface of end 582 engage the threads on surface 578. As the threads on the outer surface of end 582 engage the threads on surface 578, member 580 translates relative to end 566, in the direction shown by arrow C, into passageway 579. Member 580 is translated relative to end 566, in the direction shown by arrow C, until the outer surface of end 584 engages a bottom end surface of portion 560.

End 508 is connected to fastener 12B by disposing arm 18 of fastener 12B in cavity 512 such that surface 34 of fastener 12B engages surface 520 and surface 518 engages surfaces 26, 28 of fastener 12B. A setscrew 44B is positioned in recess 546 such that the threads on surface 42 of setscrew 44B are aligned with the threads on surfaces 38, 40 of fastener 12B. Setscrew 44B is rotated about axis A in a first direction, such as, for example, clockwise or counterclockwise, such that the thread forms on surfaces 38, 40 of fastener 12B engage the thread form on surface 42 of setscrew 44B, causing setscrew 44B to move distally relative to receiver 14 of fastener 12B, as shown by arrow B in FIG. 11. As setscrew 44B translates, in the direction shown by arrow B, a lower end surface of setscrew 44B engages surface 550 such that translating setscrew 44B, in the direction shown by arrow B, also causes end 508 to translate relative to fastener 12B, in the direction shown by arrow B. Setscrew 44B is rotated in the first direction until surface 552 engages surface 62 of rod 24B to fix rod 24B relative to receiver 14 of fastener 12B.

End 508 is rotatably fixed with end 606 by positioning end 606 relative to extension 590 such that aperture 600 and cavities 612,616 are aligned or coaxial. Pin 602 is then inserted into cavity 616 and is translated toward cavity 612. Pin 602 is translated toward cavity 612 until at least a portion of pin 602 is positioned within cavity 612. End stirrup 502 may be rotated relative to end stirrup 508 about portion 614 to adjust the position of end stirrup 502 relative to end stirrup 508.

Figure 12:
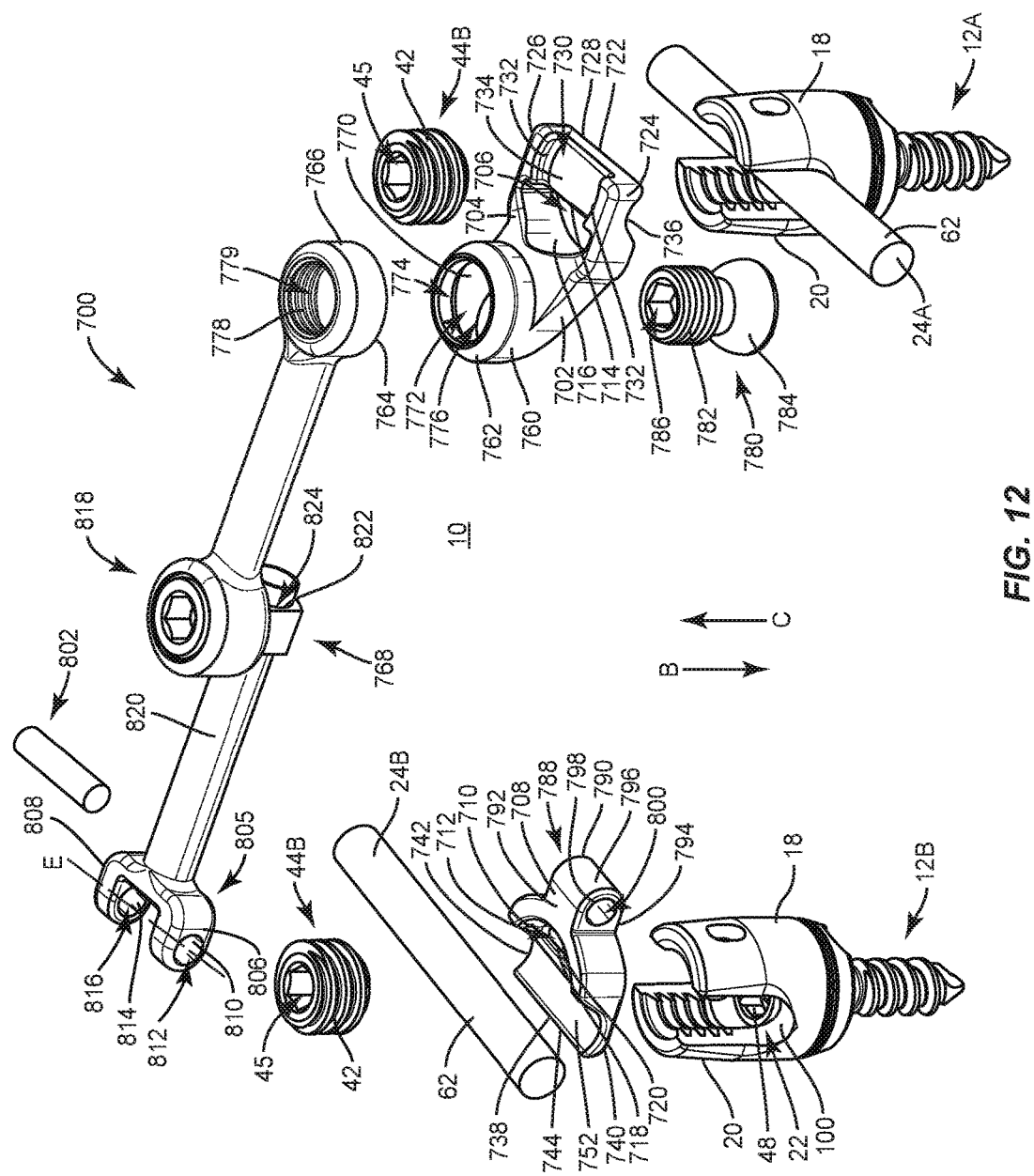
FIG. 12 is a perspective view of components of one embodiment of a system in accordance with the principles of the present disclosure.

In one embodiment, as shown in FIG. 12, system 10, similar to the systems and methods described with regard to FIG. 11, includes a spinal construct comprising fasteners 12A, 12B and rods 24A, 24B. A connecting element 700 extends between an end stirrup 702 and an opposite end stirrup 708. End stirrup 702 includes an inner surface 704 defining a cavity 706 configured for disposal of arm 18 or arm 20 of fastener 12A such that surface 704 matingly engages arm 18 or arm 20 of fastener 12A. End stirrup 708 includes an inner surface 710 defining a cavity 712 configured for disposal of an arm 18 or an arm 20 of fastener 12B such that surface 710 matingly engages arm 18 or arm 20 of fastener 12B.

Cavity 706 is defined by a planar surface 714 and an arcuate surface 716 that faces surface 714 such that cavity 706 has a hemispherical configuration. Cavity 712 is defined by a planar surface 718 that faces opposite surface 716 and an arcuate surface 720 that faces surface 718 such that cavity 712 has a hemispherical configuration.

End stirrup 702 includes a bridge 722 extending between an end 724 and an end 726. Bridge 722 has a width defined by the distance between surface 714 and an opposite planar end surface 728. Bridge 722 includes a recess 730 defined by arcuate side surfaces 732 that face one another and a planar upper surface 734 of end 702 that faces opposite an implant engaging surface 736 of end stirrup 702. Surface 736 is concavely curved between surfaces 714, 728 and is configured to engage surface 62 of rod 24A when rod 24A is disposed in cavity 22 of fastener 12A to fix rod 24A relative to receiver 14 of fastener 12A.

End stirrup 702 includes a connecting portion 760 opposite bridge 722. Portion 760 includes a tapered upper surface 762 configured to engage a tapered bottom surface 764 of an end 766 of a linkage, such as, for example, a connecting portion 768. Portion 760 includes an unthreaded inner surface 770 defining a channel 772 having openings 774, 776 at top and bottom ends of portion 760, respectively. End 766 includes a threaded inner surface 778 defining a passageway 779.

To rotatably fix end 766 with portion 760, a coupling member 780 having an end 782 with a threaded outer surface and an end 784 with an unthreaded outer surface is bottom-loaded into channel 772 such that end 782 translates, in the direction shown by arrow C, through opening 776 toward opening 774. Member 780 is translated, in the direction shown by arrow C, until the threads on the outer surface of end 782 are aligned with the threads on surface 778. Member 780 is rotated in a first direction, such as, for example, clockwise or counterclockwise, such that the threads on the outer surface of end 782 engage the threads on surface 778. As the threads on the outer surface of end 782 engage the threads on surface 778, member 780 translates relative to end 766, in the direction shown by arrow C, into passageway 779. Member 780 is translated relative to end 766, in the direction shown by arrow C, until the outer surface of end 784 engages a bottom end surface of portion 760.

End 708 includes a bridge 738 extending between an end 740 and an end 742. Bridge 738 has a width defined by the distance between surface 718 and an opposite planar end surface 744. Bridge 738 includes an implant engaging surface 752 that faces opposite surface 100 of fastener 12B. Surface 752 is concavely curved between surfaces 718, 744 and is configured to engage surface 62 of rod 24B when rod 24B is disposed in cavity 22 of fastener 12B to fix rod 24B relative to receiver 14 of fastener 12B.

End 708 includes a connecting portion 788 opposite bridge 738. Portion 788 includes an extension 790 including a planar surface 792 extending perpendicular to axis A and a planar surface 794 extending perpendicular to axis A such that surfaces 792, 794 are parallel to one another. Extension 790 includes an arcuate surface 796 extending between surfaces 792, 794. Extension 790 includes an inner surface 798 defining an aperture 800 having a cylindrical cross-sectional configuration that extends perpendicular to axis A. Aperture 800 is configured for removable disposal of a pin 802 to rotatably fix an end 804 of portion 768.

End 804 includes a pair of spaced apart arms 806, 808 such that extension 790 may be positioned between arms 806, 808. Arm 806 includes an inner surface 810 defining a cavity 812 having a cylindrical cross-sectional configuration and extending perpendicular to axis A and parallel to aperture 800. Arm 806 includes an inner surface 814 defining a cavity 816 having a cylindrical cross-sectional configuration and extending perpendicular to axis A and parallel to aperture 800. Cavity 812 is aligned with cavity 816.

To rotatably fix end 806 with extension 790, end 806 is positioned relative to extension 790 such that aperture 800 and cavities 812, 816 are aligned or coaxial. Pin 802 is then inserted into cavity 816 and is translated toward cavity 812. Pin 802 is translated toward cavity 812 until at least a portion of pin 802 is positioned within cavity 812. This configuration allows end 708 to rotate or pivot relative to end 806 about an axis E defined by cavities 812, 816. In one embodiment, pin 802 is inserted into cavity 812 and is translated toward cavity 816. Pin 802 is translated toward cavity 816 until at least a portion of pin 802 is positioned within cavity 816.

Portion 768 spans between ends 766, 806 and includes an intermediate portion 818 that connects end 766 with end 806 such that end 766 is rotatable relative to end 806. In some embodiments, end 804 includes a shaft 820 and end 766 includes a body having an inner surface 822 defining a through hole 824 configured for slidable disposal of shaft 820 to allow the length of portion 768 to be adjusted, depending upon, for example, the distance between fasteners 12A, 12B.

End 702 is connected to fastener 12A by disposing arm 20 of fastener 12A in cavity 706 such that surface 36 of fastener 12A engages surface 716 and surface 714 engages surfaces 30, 32 of fastener 12A. A setscrew 44A is positioned in recess 730 such that the threads on surface 42 of setscrew 44A are aligned with the threads on surfaces 38, 40 of fastener 12A. Setscrew 44A is rotated about axis A in a first direction, such as, for example, clockwise or counterclockwise, such that the thread forms on surfaces 38, 40 of fastener 12A engage the thread form on surface 42 of setscrew 44A, causing setscrew 44A to move distally relative to receiver 14 of fastener 12A, as shown by arrow B in FIG. 12. As setscrew 44A translates, in the direction shown by arrow B, a lower surface of setscrew 44A engages surface 734 such that translating setscrew 44A, in the direction shown by arrow B, also causes end 702 to translate relative to fastener 12A, in the direction shown by arrow B. Setscrew 44A is rotated in the first direction until surface 736 engages surface 62 of rod 24A to fix rod 24A relative to receiver 14 of fastener 12A.

End 708 is connected to fastener 12B by disposing arm 18 of fastener 12B in cavity 712 such that surface 34 of fastener 12B engages surface 720 and surface 718 engages surfaces 26, 28 of fastener 12B. End 708 is translated relative to fastener 12B, in the direction shown by arrow B, until surface 752 is positioned within cavity 22 of fastener 12B. In one embodiment, end 708 is translated relative to fastener 12B, in the direction shown by arrow B, until surface 740 engages surface 100 of fastener 12B. In one embodiment, end 708 is translated relative to fastener 12B, in the direction shown by arrow B, until surface 740 is positioned adjacent surface 100 of fastener 12B. Rod 24B is positioned relative to end 708 such that surface 62 of rod 24B engages surface 752. Rod 24B is in alignment with axis A when rod 24B engages surface 752 such that axis A intersects or extends through rod 24B.

A setscrew 44B is positioned between arms 18, 20 of fastener 12B such that the threads on surface 42 of setscrew 44B are aligned with the threads on surfaces 38, 40 of fastener 12B. Setscrew 44B is rotated about axis A in a first direction, such as, for example, clockwise or counterclockwise, such that the thread forms on surfaces 38, 40 of fastener 12B engage the thread form on surface 42 of setscrew 44B, causing setscrew 44B to move distally relative to receiver 14 of fastener 12B, as shown by arrow B in FIG. 12. As setscrew 44B translates, in the direction shown by arrow B, a lower end surface of setscrew 44B engages surface 62 of rod 24B such that translating setscrew 44B, in the direction shown by arrow B fixes rod 24B relative to surface 752.

End 708 is rotatably fixed with end 806 by positioning end 806 relative to extension 790 such that aperture 800 and cavities 812, 816 are aligned or coaxial. Pin 802 is then inserted into cavity 816 and is translated toward cavity 812. Pin 802 is translated toward cavity 812 until at least a portion of pin 802 is positioned within cavity 812. End 702 may be rotated relative to end 708 about portion 818 to adjust the position of end 702 relative to end 708.

Figure 13:
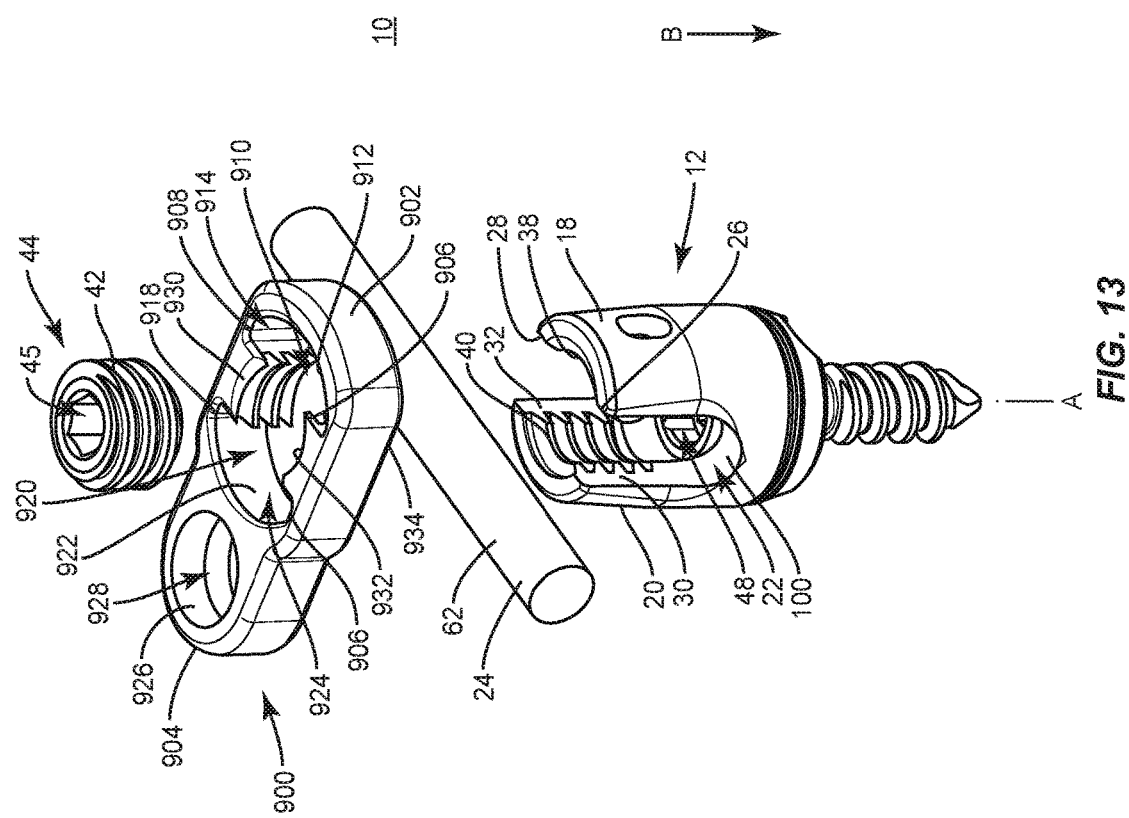
FIG. 13 is a perspective view of components of one embodiment of a system in accordance with the principles of the present disclosure.

In one embodiment, as shown in FIG. 13, system 10, similar to the systems and methods described with regard to FIGS. 1-12, includes a spinal construct comprising fastener 12 and rod 24. A connecting element 900 extends between an end 902 and an end 904. End 902 includes planar surfaces 906, 908 that extend parallel to one another and are separated by a gap 910. Surfaces 906, 908 and an arcuate surface 912 of end 902 define a cavity 914 having a hemispherical configuration configured for disposal of arm 18 or arm 20 such that surfaces 906, 908, 912 matingly engage arm 18 or arm 20.

End 902 includes planar surfaces 916, 918 that face opposite surfaces 906, 908 and extend parallel to one another. Surfaces 916, 918 are separated by a gap 920. Surfaces 916, 918 and an arcuate surface 922 of end 902 that faces surface 912 define a cavity 924 having a hemispherical configuration configured for disposal of arm 18 or arm 20 such that surfaces 916, 918, 922 matingly engage arm 18 or arm 20.

End 902 includes a threaded arcuate surface 930 extending between surfaces 908, 918 and a threaded arcuate surface 932 extending between surfaces 906, 916. Surfaces 930, 932 face one another and are configured to engage setscrew 44 to fix element 900 relative to receiver 14 of fastener 12.

End 904 includes an inner surface 926 defining a pathway 928 extending parallel to axis A having a cylindrical cross-sectional configuration configured for disposal of rod 24.

End 902 is connected to fastener 12 by disposing arm 20 of fastener 12 in cavity 924 such that surface 36 engages surface 922, surface 918 engages surface 32 and surface 916 engages surface 30. Arm 18 of fastener 12 is disposed in cavity 914 such that surface 36 engages surface 912, surface 908 engages surface 28 and surface 906 engages surface 26. Element 900 is translated relative to fastener 12, in the direction shown by arrow B, until a bottom surface 934 of element 900 engages surface 62 of rod 24 and the threads on surfaces 930, 932 are aligned or continuous with the threads on surfaces 38, 40.

To fix element 900 relative to fastener 12, setscrew 44 is positioned relative to element 900 such that the threads on surface 42 are aligned with the threads on surfaces 930, 932 and/or surfaces 38, 40. Setscrew 44 is rotated about axis A in a first direction, such as, for example, clockwise or counterclockwise, such that the thread forms on surface 42 engages the thread forms on surfaces 38, 40 of fastener 12 and/or the thread forms on surfaces 930, 932, causing setscrew 44 to move distally relative to receiver 14 of fastener 12, as shown by arrow B in FIG. 13. As setscrew 44 translates, in the direction shown by arrow B, a lower surface of setscrew 44 engages surface 62 to fix element 900 relative to fastener 12. A spinal rod may be positioned in pathway 928.

In one embodiment, as shown in FIG. 14, system 10, similar to the systems and methods described with regard to FIGS. 1-13, includes a spinal construct comprising fasteners 12A, 12B and rods 24A, 24B. A connecting element 1000 extends between an end 1002 and an end 1004 coupled to end 1002. End 1002 includes an inner surface having a planar surface 1014 and an arcuate surface 1016 that faces surface 1014. Surfaces 1014, 1016 define a cavity 1006 having a hemispherical configuration configured for disposal of arm 18 or arm 20 of fastener 12 such that surfaces 1014, 1016 matingly engage arm 18 or arm 20.

End 1002 includes a bridge 1022 extending between an end 1024 and an end 1026. Bridge 1022 has a width defined by the distance between surface 1014 and an opposite planar end surface 1028. Bridge 1022 includes a recess 1030 defined by arcuate side surfaces 1032 that face one another and a planar upper surface 1034 of end 1002 that faces opposite an implant engaging surface 1036 of end 1002. Surface 1036 is concavely curved between surfaces 1014, 1028 and is configured to engage surface 62 of rod 24A when rod 24A is disposed in cavity 22 of fastener 12A to fix rod 24A relative to receiver 14 of fastener 12A.

End 1004 defines a coupler including an upper arm 1038 and a lower arm 1040. Inner surfaces of arms 1038, 1040 define a C-shaped receptacle 1042 extending perpendicular to axis A that is configured for disposal of rod 24B. Arm 1038 includes an inner surface 1044 defining a threaded opening 1046 configured for disposal of a retaining element, such as, for example, setscrew 1048 to fix rod 24B in receptacle 1042.

End 1002 is connected to fastener 12A by disposing arm 18 of fastener 12A in cavity 1006 such that surface 36 of fastener 12A engages surface 1016 and surface 1014 engages surfaces 30, 32 of fastener 12A. A setscrew 44A is positioned in recess 1030 such that the threads on surface 42 of setscrew 44A are aligned with the threads on surfaces 38, 40 of fastener 12A. Setscrew 44A is rotated about axis A in a first direction, such as, for example, clockwise or counterclockwise, such that the thread forms on surfaces 38, 40 of fastener 12A engage the thread form on surface 42 of setscrew 44A, causing setscrew 44A to move distally relative to receiver 14 of fastener 12A, as shown by arrow B in FIG. 14. As setscrew 44A translates in the direction shown by arrow B, a lower surface of setscrew 44A engages surface 734 such that translating setscrew 44A, in the direction shown by arrow B, also causes end 702 to translate relative to fastener 12A, in the direction shown by arrow B. Setscrew 44A is rotated in the first direction until surface 1036 engages surface 62 of rod 24A to fix rod 24A relative to receiver 14 of fastener 12A.

Receiver 14 of fastener 12B is selectively rotated relative to shaft 16 of fastener 12B such that cavity 22 of fastener 12B is aligned with receptacle 142. In some embodiments, receiver 14 of fastener 12B is selectively rotated relative to shaft 16 of fastener 12B such that cavity 22 of fastener 12B is parallel to cavity 22 of fastener 12A. Rod 24B is side-loaded into cavity 22 of fastener 12B by translating rod 24B, in the direction shown by arrow F. Rod 24B is translated, in the direction shown by arrow F, until at least a portion of rod 24B is positioned in receptacle 1042. In one embodiment, rod 24B is side-loaded into receptacle 1042 by translating rod 24B, in the direction shown by arrow G. Rod 24B is translated, in the direction shown by arrow G, until at least a portion of rod 24B is positioned in cavity 22 of fastener 12B.

A setscrew 44B is positioned between arms 18, 20 of fastener 12B such that the threads on surface 42 of setscrew 44B are aligned with the threads on surfaces 38, 40 of fastener 12B. Setscrew 44B is rotated about axis A in a first direction, such as, for example, clockwise or counterclockwise, such that the thread forms on surfaces 38, 40 of fastener 12B engage the thread form on surface 42 of setscrew 44B, causing setscrew 44B to move distally relative to receiver 14 of fastener 12B, as shown by arrow B in FIG. 14. As setscrew 44B translates, in the direction shown by arrow B, a lower end surface of setscrew 44B engages surface 62 of rod 24B such that translating setscrew 44B, in the direction shown by arrow B, fixes rod 24B relative to cavity 22.

Setscrew 1048 is positioned in opening 1046 such that the threads on an outer surface of setscrew 1048 are aligned with the threads on surface 1044. Setscrew 1048 is rotated about axis A in a first direction, such as, for example, clockwise or counterclockwise, such that the thread form on surface 1044 engages the thread form on the outer surface of setscrew 1048, causing setscrew 1048 to move distally relative to arm 1038, as shown by arrow B in FIG. 14. As setscrew 1048 translates, in the direction shown by arrow B, a lower end surface of setscrew 1048 engages surface 62 of rod 24B such that translating setscrew 1048, in the direction shown by arrow B, fixes rod 24B relative to receptacle 1042. In one embodiment, a tip of a tool, such as, for example a driver is inserted into an opening 1049 of setscrew 1048 and the tool is used to rotate setscrew 1048 about axis A to fix rod 24B relative to element 1000.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    a fastener including a first portion comprising spaced-apart arms defining an implant cavity, the fastener including a second portion configured to penetrate tissue; and
    a member extending along a longitudinal axis between opposite first and second ends, the first end defining a cavity configured for disposal of only one of the arms, the member including a bridge having a concave implant engaging surface for disposal of a spinal rod, the bridge being configured to be positioned within the implant cavity, the second end comprising a connecting element fixable adjacent the first portion, the connecting element comprising an upper arm and a lower arm, inner surfaces of the arms defining a receptacle extending perpendicular to the longitudinal axis.

2. A spinal construct as recited in claim 1, wherein the second portion is movable relative to the first portion in one or a plurality of axes.

3. A spinal construct as recited in claim 1, wherein the implant cavity is U-shaped and configured for disposal of a spinal rod.

4. A spinal construct as recited in claim 1, wherein said longitudinal axis is a first longitudinal axis, and the fastener defines a second longitudinal axis such that the implant engaging surface is fixed within the implant cavity in alignment with the second longitudinal axis.

5. A spinal construct as recited in claim 1, wherein said longitudinal axis is a first longitudinal axis, and the fastener defines a second longitudinal axis such that the connecting element is fixed in alignment with the second longitudinal axis.

6. A spinal construct as recited in claim 1, wherein said longitudinal axis is a first longitudinal axis, and the fastener defines a second longitudinal axis such that the implant engaging surface is fixed within the implant cavity in alignment with the second longitudinal axis and the connecting element is fixed in alignment with the second longitudinal axis.

7. A spinal construct as recited in claim 1, wherein an outer surface of the member includes an orthogonal portion that defines the cavity for disposal of only one of the arms.

8. A spinal construct as recited in claim 1, wherein an inner surface of the member defines the cavity, the cavity being hemispherical for disposal of only one of the arms.

9. A spinal construct as recited in claim 1, wherein the member includes a surface that defines the cavity and is configured for mating engagement with an outer surface of only one of the arms.

10. A spinal construct as recited in claim 1, wherein the arms each have an inner threaded surface engageable with a coupling member to fix the implant engaging surface with the implant cavity.

11. A spinal construct as recited in claim 1, wherein the arms each have an inner threaded surface engageable with a coupling member to fix the connecting element therewith.

12. A spinal construct as recited in claim 1, wherein the connecting element is monolithically formed with the member.

13. A spinal construct as recited in claim 1, wherein the receptacle is C-shaped.

14. A spinal construct as recited in claim 1, wherein the upper arm defines a threaded opening configured for disposal of a retaining element.

15. A spinal construct as recited in claim 1, wherein the member includes a recess defined by arcuate side surfaces and a planar upper surface, the arcuate side surfaces facing one another, the upper surface facing opposite the implant engaging surface.

16. A spinal construct as recited in claim 1, wherein the member includes only one cavity.

17. A spinal construct comprising:
    a fastener including a receiver having spaced arms with an inner threaded surface defining an implant cavity and a threaded shaft configured for fixation with tissue; and
    a monolithic member extending along a longitudinal axis between opposite first and second ends, the first end including an inner surface defining a cavity configured for disposal of only one of the arms, the first end including a bridge having a concave implant engaging surface for disposal of a spinal rod, the bridge being configured for disposal within the implant cavity, the second end comprising a connecting element fixable adjacent the receiver, the connecting element comprising an upper arm and a lower arm, inner surfaces of the arms defining a receptacle extending perpendicular to the longitudinal axis.

18. A spinal construct as recited in claim 17, wherein said longitudinal axis is a first longitudinal axis, and the fastener defines a second longitudinal axis such that the implant engaging surface is fixed within the cavity of the receiver in alignment with the second longitudinal axis and the connecting element is fixed in alignment with the second longitudinal axis.

19. A spinal construct comprising:
a fastener including a receiver comprising spaced-apart arms, the arms defining an implant cavity, the fastener comprising a threaded shaft configured to penetrate tissue; and
a member comprising only one cavity configured for disposal of only one of the arms, the member including a bridge having a concave implant engaging surface for disposal of a spinal rod, the bridge being configured to be positioned within the implant cavity and connected to a connecting element fixable adjacent the first portion, the connecting element comprising an upper arm and a lower arm, inner surfaces of the arms defining a C-shaped receptacle, the upper arm defining a threaded opening configured for disposal of a retaining element.

20. A spinal construct comprising:
a fastener including a first portion comprising spaced-apart arms defining an implant cavity, the fastener including a second portion configured to penetrate tissue; and
a member extending along a longitudinal axis between opposite first and second ends, the member including a recess defined by arcuate side surfaces and a planar upper surface, the arcuate side surfaces facing one another, the upper surface facing opposite an implant engaging surface, the first end defining a cavity configured for disposal of only one of the arms, the member including a bridge having the implant engaging surface, the bridge being configured to be positioned within the implant cavity, the second end comprising a connecting element fixable adjacent the first portion, the connecting element comprising an upper arm and a lower arm, inner surfaces of the arms defining a receptacle extending perpendicular to the longitudinal axis.

21. A spinal construct comprising:
a fastener including a receiver having spaced-arms with an inner threaded surface defining an implant cavity and a threaded shaft configured for fixation with tissue; and
a monolithic member extending along a longitudinal axis between opposite first and second ends, the member including a recess defined by arcuate side surfaces and a planar upper surface, the arcuate side surfaces facing one another, the upper surface facing opposite an implant engaging surface, the first end including an inner surface defining a cavity configured for disposal of only one of the arms, the first end including a bridge having the implant engaging surface, the bridge being configured for disposal within the implant cavity, the second end comprising a connecting element fixable adjacent the receiver, the connecting element comprising an upper arm and a lower arm, inner surfaces of the arms defining a receptacle extending perpendicular to the longitudinal axis.

* * * * *